(12) United States Patent
Moszner et al.

(10) Patent No.: US 10,736,820 B2
(45) Date of Patent: Aug. 11, 2020

(54) MATERIALS WHICH CAN BE CURED BY CHAIN TRANSFER POLYMERIZATION

(71) Applicants: IVOCLAR VIVADENT AG, Schaan (LI); TECHNISCHE UNIVERSITÄT WIEN, Vienna (AT)

(72) Inventors: Norbert Moszner, Mauren (LI); Iris Lamparth, Grabs (CH); Urs Karl Fischer, Arbon (CH); Kai Rist, Feldkirch (AT); Peter Burtscher, Rankweil (AT); Robert Liska, Schleinbach (AT); Christian Gorsche, Vienna (AT); Konstanze Seidler, Oberrohrbach (AT)

(73) Assignees: Ivoclar Vivadent AG, Schaan (LI); Technicshe Universität Wien, Vienna (AT)

( * ) Notice: Subject to any disclaimer, the term of this patent is extended or adjusted under 35 U.S.C. 154(b) by 210 days.

(21) Appl. No.: 15/571,085

(22) PCT Filed: May 2, 2016

(86) PCT No.: PCT/EP2016/059799
§ 371 (c)(1),
(2) Date: Mar. 19, 2018

(87) PCT Pub. No.: WO2016/177680
PCT Pub. Date: Nov. 10, 2016

(65) Prior Publication Data
US 2018/0369075 A1 Dec. 27, 2018

(30) Foreign Application Priority Data
May 7, 2015 (EP) .................... 15166847

(51) Int. Cl.
*A61K 6/083* (2006.01)
*A61K 6/30* (2020.01)
*A61K 6/887* (2020.01)
*C08L 81/06* (2006.01)

(52) U.S. Cl.
CPC ............... *A61K 6/30* (2020.01); *A61K 6/887* (2020.01); *C08L 81/06* (2013.01)

(58) Field of Classification Search
CPC ............................... A61K 6/083; A61K 6/887
See application file for complete search history.

(56) References Cited

U.S. PATENT DOCUMENTS

| 2,667,469 A | 1/1954 | Sauer |
| 2,694,699 A * | 11/1954 | Laakso ............. C07C 309/65 526/234 |
| 5,932,675 A | 8/1999 | Rizzardo et al. |

FOREIGN PATENT DOCUMENTS

EP     3091037 A1 * 11/2016 ............... C08K 5/42

OTHER PUBLICATIONS

Database CA, Chemical Abstract Service, "Film-forming adhesives for teeth and bones," STN Database accession No. 105:214120, Jul. 9, 1986.
Elias, H.-G., "Macromolecules: vol. 1: Chemical Structure and Synthesis," Ed. 6, Wiley-VCH, Weinheim, pp. 299-352 (1999).
Liska, R. et al., "Biomaterials Based on Low Cytotoxic Vinyl Esters for Bone Replacement Application," Journal of Polymer Science Part A: Polymer Chemistry, 49, pp. 4927-4934, 2011.
Moad, G. et al., "Radical addition-fragmentation chemistry in polymer synthesis," Polymer 49, pp. 1079-1131, 2008, Elsevier Ltd.
International Preliminary Report on Patentability of PCT/EP2016/059799, dated Nov. 7, 2017, 7 pages.

* cited by examiner

Primary Examiner — Michael F Pepitone
(74) Attorney, Agent, or Firm — Ann M. Knab; Thad McMurray

(57) ABSTRACT

Radically polymerizable dental material, which contains at least one sulphonic acid ester of Formula 1:

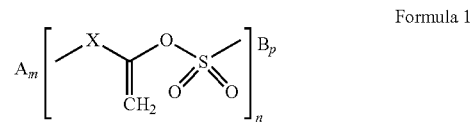

Formula 1 in which A is H, CN, an aromatic, cycloaliphatic, linear or branched aliphatic $C_1$-$C_{30}$-hydrocarbon radical or a combination thereof; X is COO— or —CON($R^1$)— or is absent; B is an aromatic, cycloaliphatic, linear or branched aliphatic $C_1$-$C_{30}$-hydrocarbon radical, or a combination thereof; $R^1$ is hydrogen or an aromatic, cycloaliphatic, linear or branched aliphatic $C_1$-$C_{10}$-hydrocarbon radical; m is an integer from 1 to 6, n is an integer from 1 to 6 and p is an integer from 1 to 6; wherein m and p cannot simultaneously be greater than 1. The compounds of Formula 1 are active as chain transfer agents in radical polymerization.

20 Claims, 4 Drawing Sheets

MATERIALS WHICH CAN BE CURED BY CHAIN TRANSFER POLYMERIZATION

CROSS-REFERENCE TO RELATED APPLICATIONS

This application is a National Stage application of International patent application PCT/EP2016/059799 filed on May 2, 2016, which claims priority to European patent application No. 15166847.2 filed on May 7, 2015, the disclosures of which are incorporated herein by reference in their entirety.

FIELD OF THE INVENTION

The present invention relates to thermally and/or light-curable radically polymerizable materials which are suitable in particular as dental materials.

BACKGROUND OF THE INVENTION

Radical polymers are formed by radical polymerization of one (homopolymer) or several radically polymerizable monomers (copolymer). Depending on the functionality of the polymerized monomers, either linear (monofunctional monomers) or crosslinked (di- or multifunctional monomers) polymers are obtained.

As is generally known, radical polymerizations can be carried out in matter (bulk polymerization), solution, suspension or emulsion. Radical-forming initiators which form radicals by thermolysis, photolysis or redox-reaction are added to initiate the polymerization. The radical polymerization proceeds according to a chain-growth mechanism in which the polymerization-initiating radicals, the so-called primary radicals, add onto the double bond of the monomers. The thus-formed initiator radicals add many further monomer molecules in a rapid growth reaction until the growth of the polymer radicals is terminated by combination or disproportionation and the finished macromolecules form.

In the case of radical polymerization chain transfers often occur. Here the polymer radical transfers an electron to a second molecule by substitution with another atom, e.g. to a monomer, solvent or polymer molecule. The newly-formed radical can again initiate a polymerization. The number average molar mass of the polymer can be regulated in a targeted manner by the addition of chain transfer agents, so-called chain regulators, (cf. H. G. Elias, Makromoleküle, Vol. 1, 6th Edition, Wiley-VCH, Weinheim etc. 199, 299-352). The known chain transfer agents include, for example, the mercaptans, which, through the transfer of an H atom, form thiyl radicals, which then initiate a new polymerization sequence.

Reagents containing double bonds which react according to a radical addition-fragmentation chain transfer mechanism (AFCT) have proved particularly worthwhile as chain transfer agents. Sulphur compounds, such as allyl sulphides, allyl sulphones, dithioesters, dithiocarbamates, xanthates and trithiocarbonates are particularly effective as AFCT reagents and are well studied (cf. G. Moad, E. Rizzardo, S. H. Thang, Polymer 49 (2008) 1079-1131). Moreover, reversible AFCT reagents (RAFT reagents), such as e.g. dithioesters, dithiocarbamates, trithiocarbonates or xanthates are known from controlled radical polymerization (cf. e.g. Moad et al., loc. cit.).

U.S. Pat. No. 2,694,699 describes the homo- and copolymerization of α-sulphonyloxyacrylates. Alkyl mercaptans can be added as chain regulators.

U.S. Pat. No. 5,932,675 discloses a process for the preparation of polymers with low molecular weight by radical polymerization, wherein the molecular weight is controlled by the addition e.g. of α-(t-butanethiomethyl) styrene as chain transfer reagent.

The use of the known transfer-active compounds makes it possible to control the molecular weight of the polymers but has the disadvantage that it leads to a significant reduction in the polymerization rate. The use of α-sulphonyloxyacrylates, alkyl or aryl sulphonic acid vinyl-esters as chain transfer reagents is not known.

SUMMARY OF THE INVENTION

The object of the invention is to provide dental materials and in particular coating materials, prosthesis materials, adhesives and composites which, when compared with known materials based on multifunctional (meth)acrylates are characterized after curing by a narrower glass transition range, an improved impact strength and a reduced polymerization shrinkage force with similar mechanical properties. Above all, the materials are to have a high reactivity and curing rate, no intrinsic colour and no unpleasant odour.

The object of the invention is to provide dental materials and in particular coating materials, prosthesis materials, adhesives and composites which, when compared with known materials based on multifunctional (meth)acrylates are characterized after curing by a narrower glass transition range, an improved impact strength and a reduced polymerization shrinkage force with similar mechanical properties. Above all, the materials are to have a high reactivity and curing rate, no intrinsic colour and no unpleasant odour.

BRIEF DESCRIPTION OF THE DRAWINGS

The invention is explained in more detail below by means of figures and embodiment examples.

DETAILED DESCRIPTION

Figure 1:
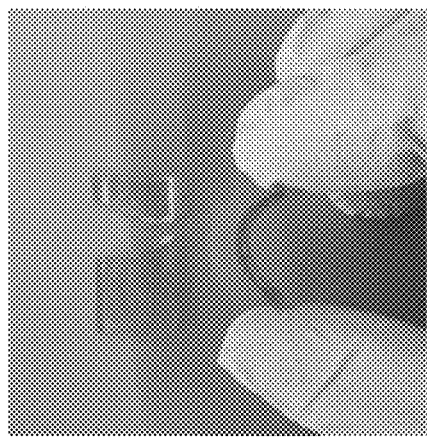
FIG. 1 is a photograph of a bending test with a polymer according to the invention.

This object is achieved according to the invention by radically polymerizable compositions which contain at least one sulphonic acid ester of Formula 1:

This object is achieved according to the invention by radically polymerizable compositions which contain at least one sulphonic acid ester of Formula 1:

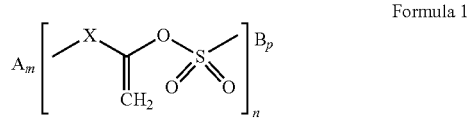

Formula 1 in which the variables have the following meanings:

A H, CN, a cycloaliphatic, linear or branched aliphatic $C_1$-$C_{30}$-hydrocarbon radical, which can be substituted by one or more, preferably 1 to 6, particularly preferably 1 to 3 substituents, preferably —$CH_3$, —$C_2H$, —OH, —$OCH_3$ and/or —O—$COCH_3$, which can be interrupted by one or more, preferably 1 to 4, particularly preferably 1 to 2 urethane groups, ester groups, O and/or S and which can contain 1 to 4, preferably 1 or 2 benzene groups, an aromatic $C_6$-$C_{30}$-hydrocarbon radical, which can be substituted by one or more, preferably 1 to 6, particularly preferably 1 to 3 substituents, preferably —$CH_3$, —$C_2H_5$, —OH, —$OCH_3$ and/or —O—$COCH_3$, or a combination thereof;

X —COO—, —CON($R^1$)— or is absent, wherein the bond to A takes place via O or N;

B a cycloaliphatic, linear or branched aliphatic $C_1$-$C_{30}$-hydrocarbon radical, which can be substituted by one or more, preferably 1 to 6, particularly preferably 1 to 3 substituents, preferably $C_1$- to $C_5$-alkyl, —OH, —O—$COCH_3$ and/or $C_1$- to $C_5$-alkoxy, which can be interrupted by one or more, preferably 1 to 4, particularly preferably 1 to 2 urethane groups, ester groups, O and/or S and which can contain 1 to 4, preferably 1 or 2 benzene groups, an aromatic $C_6$-$C_{30}$-hydrocarbon radical, which can be substituted by one or more, preferably 1 to 6, particularly preferably 1 to 3 substituents, preferably $C_1$- to $C_5$-alkyl, —OH, —O—$COCH_3$ and/or $C_1$- to $C_5$-alkoxy, or tosyl, or a combination thereof;

$R^1$ hydrogen, a cycloaliphatic, linear or branched aliphatic $C_1$-$C_{10}$-hydrocarbon radical, which can be interrupted by one or more, preferably 1 to 4, particularly preferably 1 to 2 oxygen atoms, and which can be substituted by one or more, preferably 1 to 4, particularly preferably 1 to 2 OH groups, or an aromatic $C_6$-$C_{10}$-hydrocarbon radical, which can be substituted by one or more, preferably 1 to 4, particularly preferably 1 to 2 OH groups;

m an integer from 1 to 6;

n an integer from 1 to 6;

p an integer from 1 to 6; wherein m and p cannot simultaneously be greater than 1 and wherein, if m=1, p=n, and if p=1, m=n.

The formula extends only to those compounds which are compatible with the theory of chemical valence. For example, if A is a $C_1$ radical, m can at most be 4. The indication that a radical is interrupted by one or more urethane groups, O atoms, S atoms etc. is to be understood to mean that these groups are inserted in each case into the carbon chain of the radical. These groups are thus bordered on both sides by C atoms and cannot be terminal. $C_1$ radicals cannot be interrupted. In contrast, the indication that a radical contains a benzene group means that this group can also be terminal, wherein optionally remaining yl positions are saturated by H. By combinations is meant groups which are composed of the meanings specified in each case, for example of aromatic and aliphatic radicals, such as e.g. -Ph-$CH_2$-Ph-, or of several aromatic radicals, such as e.g. -Ph-Ph-, or of aromatic and/or aliphatic radicals and others of the named groups, such as e.g. -Ph-O-Ph- (Ph=phenyl).

The compounds of Formula 1 are active in the radical polymerization as chain transfer agents and the use thereof as chain regulators is likewise a subject-matter of the invention.

Formula 1 is to be understood to mean that n of the group in brackets are bonded to the radical A or the radical B. In the first case, m is equal to 1 and p is equal to n. In this case, Formula 1 can be simplified to form Formula 2:

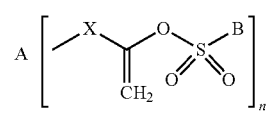

Formula 2

In Formula 2, 1 to 6 of the group in brackets are bonded in each case to A. In this case, A is an n-valent radical and B is a monovalent radical. In the case of Formula 2, the variables preferably have the following meanings:

A H, CN, an aliphatic, linear or branched $C_1$-$C_{30}$-hydrocarbon radical, which can be substituted by one or more, preferably 1 to 4, particularly preferably 1 to 2 substituents, which are selected from $CH_3$, —$C_2H_5$, —OH, —$OCH_3$ and/or —O—$COCH_3$, which can be interrupted by one or more, preferably 1 to 4, particularly preferably 1 to 2 urethane groups, ester groups, O and/or S and which can contain 1 to 4, preferably 1 or 2 benzene groups, preferably 1,4-phenylene groups, an aromatic $C_6$-$C_{30}$-hydrocarbon radical, which can be substituted by one or more, preferably 1 to 4, particularly preferably 1 to 2 substituents, which are selected from $CH_3$, —$C_2H$, —OH, —$OCH_3$ and/or —O—$COCH_3$, or a combination thereof;

X —COO—, —CON($R^1$)— or is absent, wherein the bond to A takes place via O or N, and wherein X is preferably absent, if A is an aromatic hydrocarbon radical or CN;

B an aliphatic, linear or branched $C_1$-$C_{20}$-hydrocarbon radical, which can be substituted by one or more, preferably 1 to 3, particularly preferably 1 to 2 substituents, preferably $C_1$- to $C_5$-alkyl and/or $C_1$- to $C_5$-alkoxy, which can be interrupted by one or more, preferably 1 to 4, particularly preferably 1 to 2 urethane groups, ester groups, O or S and which can contain 1 to 4, preferably 1 or 2 benzene groups, preferably 1,4-phenylene groups, an aromatic $C_6$-$C_{18}$-hydrocarbon radical, which can be substituted by one or more, preferably 1 to 3, particularly preferably 1 to 2 substituents, preferably $C_1$- to $C_5$-alkyl and/or $C_1$- to $C_5$-alkoxy, tosyl or a combination thereof;

$R^1$ hydrogen or a linear or branched aliphatic $C_1$-$C_{10}$-hydrocarbon radical, which can be interrupted by one or more, preferably 1 to 4, particularly preferably 1 to 2 oxygen atoms and which can be substituted by one or more, preferably 1 to 4, particularly preferably 1 to 2 OH groups;

n an integer from 1 to 6.

Compounds of Formula 2 are particularly preferred in which the variables have the following meanings:

A an aliphatic linear or branched $C_1$-$C_{20}$-hydrocarbon radical, which can be interrupted by one or more, preferably 1 to 4, particularly preferably 1 to 2 1,4-phenylene groups, urethane groups, ester groups, O and/or S and which can be substituted by one or more, preferably 1 to 4, particularly preferably 1 to 2 OH groups, or a phenyl radical which can be substituted by one or more, preferably 1 to 3, particularly preferably 1 to 2 substituents, preferably —$CH_3$, and/or —$OCH_3$;

X —O—CO— or is absent, wherein the bond to A takes place via O and wherein X is preferably absent, if A is an aromatic hydrocarbon radical or CN;

B an aliphatic linear or branched $C_1$-$C_{20}$-hydrocarbon radical, which can be interrupted by one or more, preferably 1 to 4, particularly preferably 1 to 2 oxygen atoms and which can contain 1 to 4, preferably 1 or 2 benzene groups, preferably 1,4-phenylene groups, or a phenyl radical, which can be substituted by 1 or 2, preferably 1 —OCH₃ or preferably —CH₃ group(s);
n 1 or 2.

Compounds of Formula 2 are quite particularly preferred in which the variables have the following meanings:
A an aliphatic linear or branched $C_1$-$C_{12}$-hydrocarbon radical, which can be interrupted by 1 to 2 urethane groups, ester groups, O and/or S, which can contain 1 to 2 benzene groups, preferably 1,4-phenylene groups, and which can be substituted by 1 to 2 OH groups, or a phenyl radical, which can be substituted by —CH₃, and/or —OCH₃;
X —O—CO— or is absent, wherein the bond to A takes place via O and wherein X is preferably absent, if A is an aromatic hydrocarbon radical or CN;
B an aliphatic linear or branched $C_1$-$C_6$-hydrocarbon radical, which can be interrupted by an oxygen atom and can contain a benzene group, preferably a 1,4-phenylene group, or a phenyl radical or p-methyl phenyl radical;
n 1 or 2.

In particular, those compounds of Formula 2 are preferred in which the variables have the following meanings:
A an aliphatic linear $C_1$-$C_8$-hydrocarbon radical, which can be interrupted by 1 to 2 urethane groups or O, or a phenyl radical;
X —O—CO—, wherein the bond to A takes place via O and wherein X is preferably absent, if A is an aromatic hydrocarbon radical or CN;
B an aliphatic linear $C_1$-$C_3$-hydrocarbon radical, a phenyl radical or p-methyl phenyl radical;
n 1 or 2.

If several of the group in brackets are bonded to the radical B, p is equal to 1 and m is equal to n. In this case, Formula 1 can be simplified to form Formula 3:

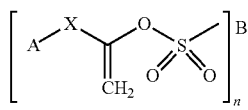

Formula 3

In Formula 3, 1 to 6 of the group in brackets are bonded in each case to B. In this case A is a monovalent radical and B is an n-valent radical. In the case of Formula 3 the variables preferably have the following meanings:
A hydrogen, —CN, a phenyl radical, which can be substituted by one or more, preferably 1 to 3, particularly preferably 1 to 2 substituents, preferably —CH₃, —C₂H₅, —OH, —OCH₃ and/or —O—COCH₃, or an aliphatic linear or branched $C_1$-$C_{20}$-hydrocarbon radical, which can be interrupted by one or more, preferably 1 to 4, particularly preferably 1 to 2 urethane groups, ester groups, O and/or S, which can contain 1 to 4, preferably 1 or 2 benzene groups, preferably 1,4-phenylene groups and which can be substituted by one or more, preferably 1 to 4, particularly preferably 1 to 2 OH groups;
B a cycloaliphatic, linear or branched aliphatic $C_1$-$C_{20}$-hydrocarbon radical, which can be substituted by one or more, preferably 1 to 4, particularly preferably 1 to 2 OH groups, which can be interrupted by one or more, preferably 1 to 4, particularly preferably 1 to 2 urethane groups, ester groups, O and/or S and which can contain 1 to 4, preferably 1 or 2 benzene groups,
an aromatic $C_6$-$C_{18}$-hydrocarbon radical, which can be substituted by one or more, preferably 1 to 4, particularly preferably 1 to 2 OH groups, or a combination thereof;
X —COO— or —CON(R¹)— or is absent, wherein the bond to A takes place via O or N and wherein X is preferably absent, if A is an aromatic hydrocarbon radical or CN;
R¹ hydrogen or a linear or branched aliphatic $C_1$-$C_{10}$-hydrocarbon radical, which can be interrupted by one or more, preferably 1 to 4, particularly preferably 1 to 2 oxygen atoms and which can be substituted by one or more, preferably 1 to 4, particularly preferably 1 to 2 OH groups;
n an integer from 2 to 4.

Compounds of Formula 3 are particularly preferred in which the variables have the following meanings:
A H, a phenyl radical, which can be substituted by one or more substituents, preferably —CH₃, —OH, —OCH₃, or an aliphatic, linear or branched $C_1$-$C_8$-hydrocarbon radical, which can be interrupted by one or more, preferably 1 to 4, particularly preferably 1 to 2 urethane groups, ester groups and/or O;
B an aliphatic, linear or branched $C_1$-$C_{10}$-hydrocarbon radical, which can be interrupted by one or more, preferably 1 to 4, particularly preferably 1 to 2 O atoms and which can contain 1 to 4, preferably 1 or 2 benzene groups, preferably 1,4-phenylene groups, an aromatic $C_6$-$C_{10}$-hydrocarbon radical, or a combination thereof;
X —COO— or is absent, wherein the bond to A takes place via O and wherein X is preferably absent, if A is an aromatic hydrocarbon radical or CN; and
n 2.

Compounds of Formula 3 are quite particularly preferred in which the variables have the following meanings:
A H, a phenyl radical, which can be substituted by —CH₃, —OH, —OCH₃, or an aliphatic, linear or branched $C_1$-$C_8$-hydrocarbon radical, which can be interrupted by one or more, preferably 1 to 4, particularly preferably 1 to 2 urethane groups, ester groups and/or O;
B an aliphatic, linear or branched $C_1$-$C_4$-hydrocarbon radical, which can be interrupted by 1 to 2 O atoms and which can contain 1 to 2 benzene groups, preferably 1,4-phenylene groups,
an aromatic $C_6$-$C_{10}$-hydrocarbon radical, preferably phenyl or naphthyl,
or a combination thereof, preferably -Ph-CH₂-Ph-; -Ph-O-Ph- or -Ph-Ph-;
X —COO— or is absent, wherein the bond to A takes place via O and wherein X is preferably absent, if A is an aromatic hydrocarbon radical or CN; and
n 2.

In particular, those compounds of Formula 3 are preferred in which the variables have the following meanings:
A a phenyl radical or an aliphatic linear or branched $C_1$-$C_3$-alkyl radical;
B an aliphatic, linear $C_1$-$C_4$-hydrocarbon radical, which can be interrupted by an O atom and which can contain a benzene group, preferably 1,4-phenylene group, phenyl, -Ph-Ph-, -Ph-CH₂-Ph-, -Ph-O-Ph- or naphthyl;
X —COO— or is absent, wherein the bond to A takes place via O; and
n 2.

For reasons of simplicity, the designations for monovalent radicals such as phenyl and naphthyl are also used herein for polyvalent radicals with more than one yl position, wherein the respective meaning can be seen from Formulae 1, 2 and 3. Phenyl (Ph) thus includes in particular phenylene and benzene-1,3,5-triyl. Naphthyl preferably represents a naphthalene-2,6-diyl radical.

Some polymerization-transfer-active compounds of Formula 1 are already known and can be prepared using known synthesis methods. For example, polymerization-transfer-active compounds of Formula 1 according to the invention can be obtained by reacting pyruvic acid derivatives with sulphonyl halides under basic conditions:

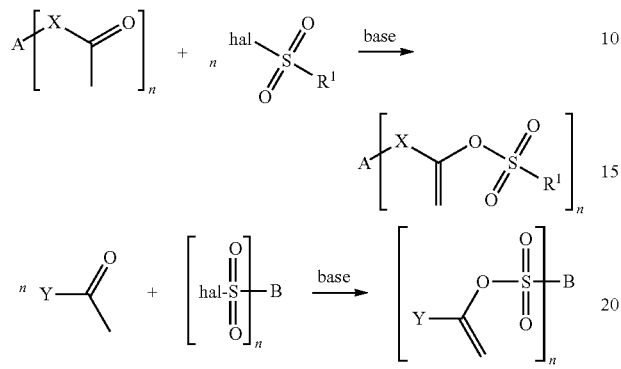

A specific example is:

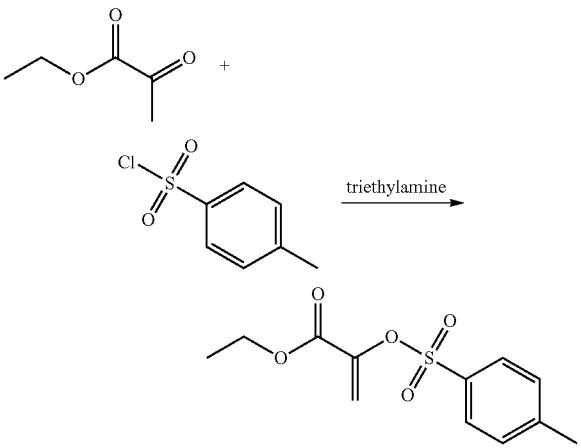

Preferred examples of the polymerization-transfer-active compounds of Formula 1 according to the invention are:

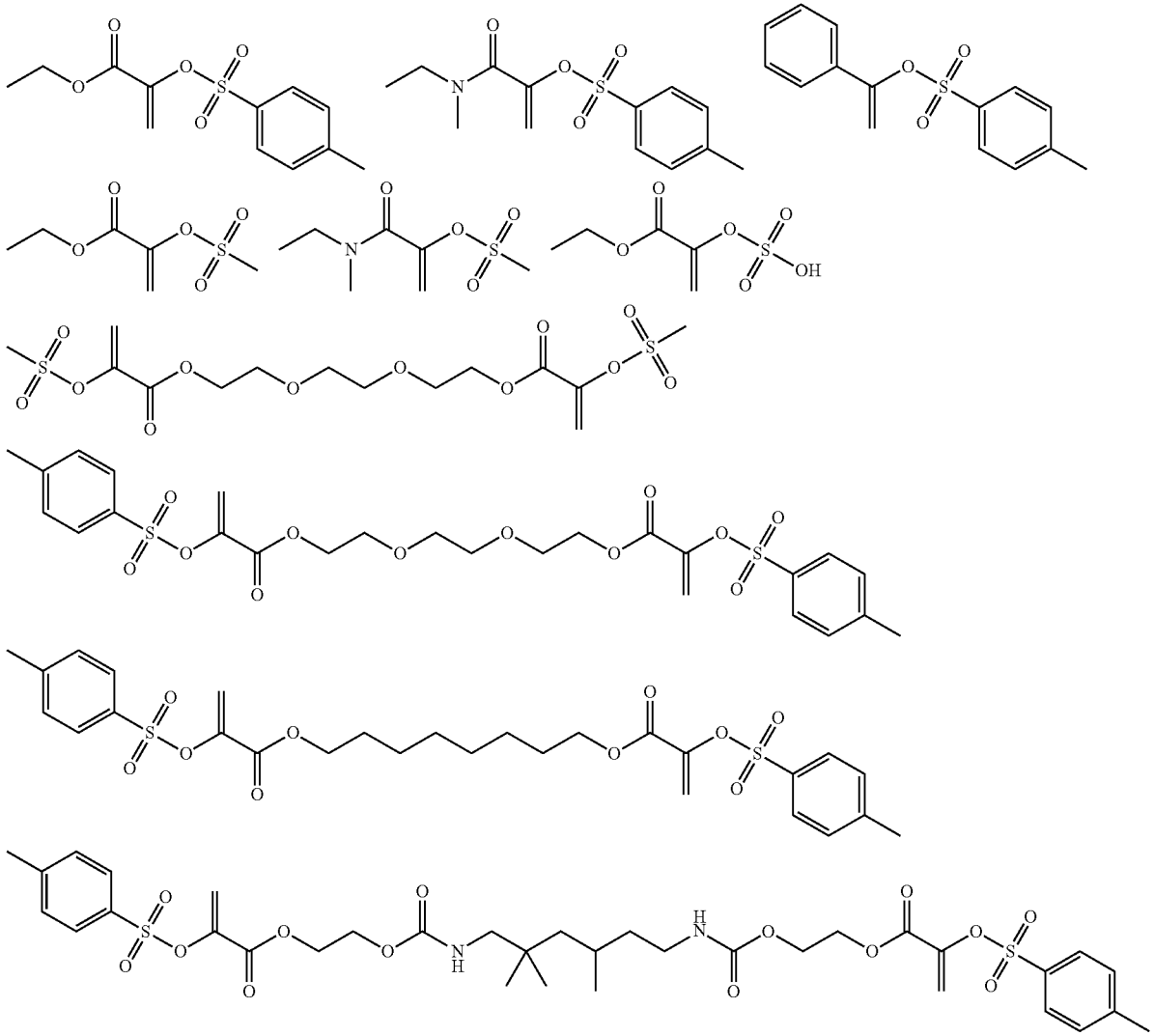

-continued
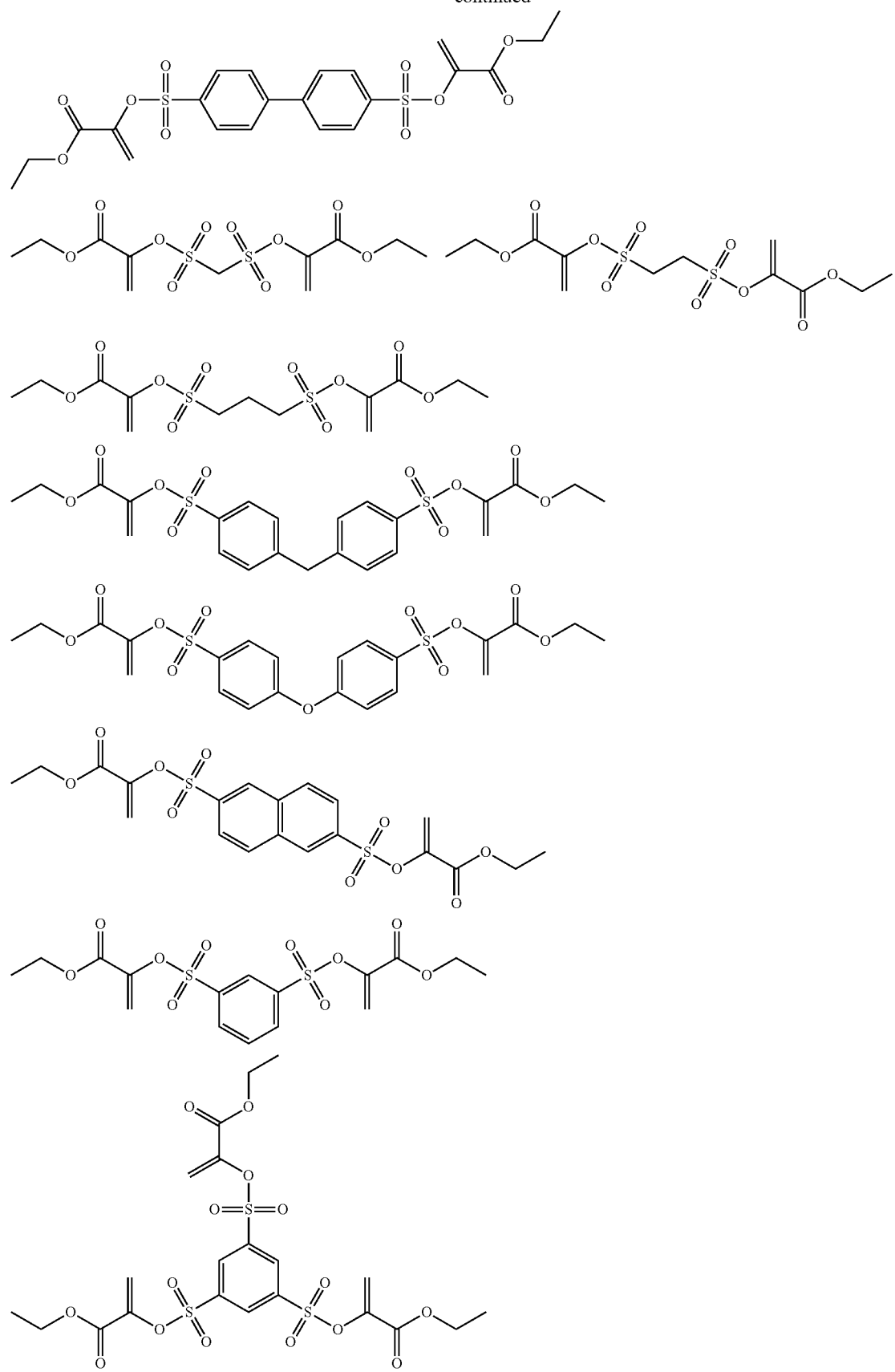

The compounds of Formula 1 according to the invention can be used advantageously as chain transfer agents for monitoring and controlling the network structure during the polymerization of mono(meth)acrylates, multifunctional (meth)acrylates and mixtures thereof. Chain transfer agents are also called transfer reagents or regulators here. In comparison with pure (meth)acrylates they yield polymer networks with a narrower glass transition, i.e. the glass transition takes place in a narrower temperature range. In addition, more homogeneous polymer networks are obtained, i.e. networks which are characterized by having a narrower distribution of the molar mass between the cross-linking points. This has the advantage that chain tensions can be better relieved by relaxation processes and that e.g. in the area of dental cements a quicker debonding-on-demand (DoD) can be effected.

In addition, it was surprisingly found that, during the polymerization of (meth)acrylates, the compounds of Formula 1 significantly reduce the glass transition temperature of the polymerized materials without appreciably lowering the polymerization rate. A reduced glass transition temperature has the advantage that the polymers can be softened at lower temperatures. This permits, e.g. in the case of adhesives and cements, a targeted debonding of the adhesive bond (debonding-on-demand).

Moreover, the polymer materials obtained are characterized by an improved impact strength, which is of great advantage e.g. in stereolithographically manufactured mouldings or in dental prostheses.

In the cross-linking polymerization e.g. of multifunctional (meth)acrylates, the compounds of Formula 1 effect a significant delay in gel formation and thus ensure a longer gel time, i.e. the 3-dimensional polymer network forms later. The extended gel time has a favourable effect on the polymerization shrinkage stress (PSS), because internal stresses can be balanced out for longer by flow processes. This leads to significantly lower shrinkage stresses, which is of great advantage e.g. in the case of complex geometries of moulded parts or dental filling composites.

The compounds of Formula 1 can therefore be used to reduce the glass transition temperature, to reduce the polymerization shrinkage force and/or to improve the impact strength of polymers. The polymerization shrinkage force is also called polymerization shrinkage stress.

According to the invention those materials are preferred which, in addition to a compound of Formula 1, additionally contain at least one radically polymerizable monomer and preferably also at least one initiator for the radical polymerization.

The molar ratio between the ethylenic unsaturations in the radically polymerizable monomers and the sulphonate groupings in the sulphonic acid esters of Formulae 1 to 3 serving as regulator is, according to the present invention, preferably at least 2:1 and in particularly preferred embodiments at least 3:1, more preferably at least 5:1 or at least 10:1, in order not to reduce the chain lengths too much through the presence of the regulator. Based on the molecular weight, preferably 50 to 99 wt.-%, more preferably 60 to 98 wt.-%, more preferably 70 to 95 wt.-% of the ethylenically unsaturated monomers are used based on the total weight of the monomers and regulators, which depends, on the one hand, on the substituents A and B in Formulae 1 to 3 and, on the other hand, on the monomers to be polymerized in each case.

Materials are particularly preferred which contain at least one multifunctional (meth)acrylate or a mixture of mono- and multifunctional (meth)acrylates as radically polymerizable monomer. By monofunctional (meth)acrylates is meant compounds with one, by polyfunctional (meth)acrylates is meant compounds with two or more, preferably 2 to 4, radically polymerizable groups. According to a quite particularly preferred embodiment, the compositions according to the invention contain at least one dimethacrylate or a mixture of mono- and dimethacrylates. Materials which contain mono- and multifunctional (meth)acrylates as radically polymerizable monomer are suitable in particular as dental materials, wherein methacrylates are preferred for materials which are cured intraorally.

Examples of particularly suitable mono- or multifunctional (meth)acrylates are methyl, ethyl, 2-hydroxyethyl, butyl, benzyl, tetrahydrofurfuryl or isobornyl (meth)acrylate, p-cumyl-phenoxyethylene glycol methacrylate (CMP-1E), bisphenol A di(meth)acrylate, bis-G(M)A (an addition product of (meth)acrylic acid and bisphenol A diglycidyl ether), ethoxylated or propoxylated bisphenol A di(meth) acrylate, such as e.g. the bisphenol A dimethacrylate SR-348c (Sartomer) with 3 ethoxy groups or 2,2-bis[4-(2-(meth)-acryloxypropoxy)phenyl]propane, UD(M)A (an addition product of 2-hydroxyethyl (meth)acrylate and 2,2, 4- or 2,4,4-trimethylhexamethylene-1,6-diisocyanate), di-, tri- or tetraethylene glycol di(meth)acrylate, trimethylolpropane tri(meth)acrylate, pentaerythritol tetra(meth)acrylate, as well as glycerol di- and tri(meth)acrylate, 1,4-butanediol di(meth)acrylate, 1,10-decanediol di(meth)acrylate ($D_3MA$), 1,12-dodecanediol di(meth)acrylate or oligomeric polyether, polyester, epoxy, silicone or urethane (meth) acrylates.

In addition, thermo- or photolabile di(meth)acrylates, such as e.g. the addition product of 2 mol 2-acetoacetoxyethyl methacrylate and 1 mol 2,2,4- or 2,4,4-trimethylhexamethylene-1,6-diisocyanate (thermolabile) or methacrylic acid-2-[2-(4-{2-methyl-2-[2-(methacryloyloxy)-ethylcarbamoyloxy]-propionyl}-phenoxy)-ethoxycarbonylamino]-ethyl ester are also suitable. Mixtures of thermo- or photolabile monomers and compounds of Formula 1 are suitable in particular for materials with debonding-on-demand properties.

Preferably, benzophenone, benzoin and derivatives thereof or α-diketones or derivatives thereof, such as 9,10-phenanthrenequinone, 1-phenyl-propane-1,2-dione, diacetyl or 4,4'-dichlorobenzil are used to initiate radical photopolymerization. Camphorquinone (CQ) and 2,2-dimethoxy-2-phenyl-acetophenone are particularly preferably used, and α-diketones in combination with amines as reducing agent, such as e.g. 4-(dimethylamino)-benzoic acid ester (EDMAB), N,N-dimethylaminoethyl methacrylate, N,N-dimethyl-sym.-xylidine or triethanolamine are quite particularly preferably used. Norrish type I photoinitiators are also well suited, above all acyl or bisacyl phosphine oxides, and in particular monoacyltrialkyl- or diacyldialkylgermanium compounds, such as e.g. benzoyltrimethylgermanium, dibenzoyldiethylgermanium or bis(4-methoxybenzoyl)diethylgermanium (MBDEGe). Mixtures of the different photoinitiators can also be used advantageously, such as e.g. bis(4-methoxybenzoyl)diethyl germanium in combination with camphorquinone and 4-dimethylaminobenzoic acid ethyl ester.

Thermal initiators, such as azo compounds, e.g. azobisisobutyronitrile, or peroxides, e.g. dibenzoyl peroxide as well as benzopinacol and 2,2'-dialkylbenzopinacols are suitable in particular as initiators for hot curing. Redox-initiator combinations ("redox initiator") such as e.g. combinations of benzoyl peroxide with N,N-dimethyl-sym.-xylidine or N,N-dimethyl-p-toluidine are preferably used as initiators for a polymerization carried out at room temperature. Moreover, redox systems consisting of peroxides and reductants such as e.g. ascorbic acid, barbiturates or sulphinic acids, are also particularly suitable.

According to a preferred embodiment, the materials, in particular dental materials, according to the invention additionally contain organic or preferably inorganic particulate filler, particularly preferably one or more inorganic particulate fillers. Mixtures which contain monomers, preferably multifunctional (meth)acrylates, mixtures thereof or mixtures of multifunctional and monofunctional (meth)acrylates, and fillers are called composites.

Particularly suitable are fillers based on oxides with a particle size of from 0.010 to 15 µm, such as $SiO_2$, $ZrO_2$ and $TiO_2$ or mixed oxides of $SiO_2$, $ZrO_2$, ZnO and/or $TiO_2$, nanoparticulate or microfine fillers with a particle size of from 10 to 300 nm, such as pyrogenic silica or precipitated silica as well as glass powders with a particle size of from 0.01 to 15 µm, preferably from 0.2 to 1.5 µm, such as quartz, glass ceramic or X-ray opaque glass powders of e.g. barium or strontium aluminium silicate glasses, and X-ray opaque fillers with a particle size of from 0.2 to 5 µm, such as ytterbium trifluoride, tantalum(V) oxide, barium sulphate or mixed oxides of $SiO_2$ with ytterbium(III) oxide or tantalum (V) oxide. Fibrous fillers, nanofibers or whiskers are also not excluded. Unless otherwise indicated, all particle sizes are weight-average particle sizes.

The fillers are divided, according to particle size, into macrofillers and microfillers. Macrofillers are obtained by grinding quartz, X-ray opaque glasses, borosilicates or ceramic, are of a purely inorganic nature and mostly consist of splinter-like parts. Macrofillers with an average particle size of from 0.2 to 10 µm are preferred. Pyrogenic $SiO_2$ or precipitated silica, or mixed oxides, e.g. $SiO_2$—$ZrO_2$, which can be accessed by hydrolytic co-condensation of metal alkoxides, are preferably used as microfillers. The microfillers preferably have an average particle size of from approx. 5 to 100 nm.

To improve the bond between the filler particles and the cross-linked polymerization matrix, $SiO_2$-based fillers can be surface-modified with (meth)acrylate-functionalized silanes. An example of such silanes is 3-(meth)acryloyloxypropyltrimethoxysilane. To surface-modify non-silicate fillers, e.g. of $ZrO_2$ or $TiO_2$, functionalized acidic phosphates, such as e.g. 10-(meth)acryloyloxydecyl dihydrogen phosphate can also be used.

The fill level is geared to the desired intended use. Filling composites preferably have a filler content of 75-90 wt.-% and composite cements have a filler content of 50-75 wt.-%.

Optionally, the compositions used according to the invention can contain further additives, above all stabilizers, dyes, microbiocidal active ingredients, fluoride-ion-releasing additives, propellants, optical brighteners, plasticizers or UV absorbers.

The dental materials according to the invention preferably contain 0.5 to 40 wt.-%, preferably 2.0 to 30 wt.-% and particularly preferably 5.0 to 30 wt.-% of at least one compound of general formula 1.

In addition, the dental materials preferably also contain 0.01 to 5.0 wt.-%, preferably 0.1 to 5.0 wt.-% and particularly preferably 0.1 to 3.0 wt.-% initiator(s) for the radical polymerization, particularly preferably a photoinitiator, and quite particularly preferably also 5 to 80 wt.-%, preferably 10 to 70 wt.-% and particularly preferably 10 to 60 wt.-% multifunctional (meth)acrylate(s).

Furthermore, the dental materials according to the invention preferably contain 0 to 90 wt.-%, preferably 0 to 80 wt.-% and particularly preferably 0 to 70 wt.-% filler(s), wherein the filler content is matched to the planned use of the materials, as described above.

Depending on the desired intended use, the dental materials according to the invention can also advantageously contain a solvent, preferably 0 to 80 wt.-%, particularly preferably 0 to 60 wt.-% and quite particularly preferably 0 to 40 wt.-% solvent. Preferred solvents are water, ethanol, polyethylene glycol and mixtures thereof.

In addition, the dental materials according to the invention can contain further additive(s), preferably in a quantity of from 0 to 5 wt.-%, particularly preferably 0 to 3 wt.-% and quite particularly preferably 0.2 to 3 wt.-%.

According to the invention, dental materials which contain the following components are particularly preferred:
(a) 0.5 to 40 wt.-%, preferably 1.0 to 30 wt.-% and particularly preferably 2.0 to 30 wt.-% of at least one compound of general formula 1,
(b) 0.01 to 5.0 wt.-%, preferably 0.1 to 5.0 wt.-% and particularly preferably 0.1 to 3.0 wt.-% initiator(s),
(c) 5 to 80 wt.-%, preferably 10 to 70 wt.-% and particularly preferably 10 to 60 wt.-% multifunctional (meth) acrylate(s).

The dental materials preferably contain in addition:
(d) 0 to 50 wt.-%, preferably 0 to 40 wt.-% and particularly preferably 0 to 30 wt.-% monofunctional (meth) acrylate(s),
(e) 0 to 95 wt.-%, preferably 5 to 85 wt.-% and particularly preferably 5 to 80 wt.-% filler(s),
(f) 0 to 5 wt.-%, preferably 0 to 3 wt.-% and particularly preferably 0.2 to 3 wt.-% additive(s) and
(g) 0 to 80 wt.-%, preferably 0 to 60 wt.-% and particularly preferably 0 to 40 wt.-% solvent, in particular water, ethanol and/or polyethylene glycol.

Dental materials for use as prosthesis materials, adhesives or coating materials preferably contain:
(a) 0.5 to 40 wt.-%, preferably 1.0 to 30 wt.-% and particularly preferably 2.0 to 30 wt.-% of at least one compound of general formula 1,
(b) 0.01 to 5.0 wt.-%, preferably 0.1 to 5.0 wt.-% and particularly preferably 0.1 to 3.0 wt.-% initiator(s),
(c) 5 to 80 wt.-%, preferably 10 to 80 wt.-% and particularly preferably 15 to 80 wt.-% multifunctional (meth) acrylate(s),
(d) 0 to 40 wt.-%, preferably 0 to 30 wt.-% and particularly preferably 0 to 20 wt.-% monofunctional (meth) acrylate(s),
(e) 0 to 5 wt.-%, preferably 0 to 3 wt.-% and particularly preferably 0.2 to 3 wt.-% additive(s),
(f) 0 to 60 wt.-%, preferably 0 to 50 wt.-% and particularly preferably 0 to 40 wt.-% solvent, preferably water, ethanol and/or polyethylene glycol.

Dental materials for use as composites, in particular as filling composites and cements, preferably contain:
(a) 0.5 to 30 wt.-%, preferably 1.0 to 30 wt.-% and particularly preferably 2.0 to 20 wt.-% of at least one compound of general formula 1,
(b) 0.01 to 5.0 wt.-%, preferably 0.1 to 5.0 wt.-% and particularly preferably 0.1 to 3.0 wt.-% initiator(s),
(c) 5 to 50 wt.-%, preferably 10 to 40 wt.-% and particularly preferably 10 to 30 wt.-% multifunctional (meth) acrylate(s),
(d) 0 to 30 wt.-%, preferably 0 to 20 wt.-% and particularly preferably 0 to 10 wt.-% monofunctional (meth) acrylate(s),
(e) 5 to 85 wt.-%, preferably 20 to 85 wt.-% and particularly preferably 30 to 80 wt.-% filler(s), and (f) 0 to 5 wt.-%, preferably 0 to 3 wt.-% and particularly preferably 0.2 to 3 wt.-% additive(s).

Dental materials for the manufacture of dental mouldings and restorations by 3D printing preferably contain:

(a) 0.5 to 50 wt.-%, preferably 0.5 to 30 wt.-% and particularly preferably 1.0 to 20 wt.-% of at least one compound of general formula 1,
(b) 0.001 to 2.0 wt.-%, preferably 0.01 to 2.0 wt.-% and particularly preferably 0.05 to 1.5 wt.-% photoinitiator(s),
(c) 1 to 40 wt.-%, preferably 5 to 40 wt.-% and particularly preferably 10 to 30 wt.-% radically polymerizable monomer(s),
(d) 30 to 90 wt.-%, preferably 40 to 90 wt.-% and particularly preferably 40 to 85 wt.-% ceramic and/or glass ceramic particles as filler(s), and
(f) optionally 0.001 to 15 wt.-%, preferably 0.1 to 15 wt.-% and particularly preferably 0.1 to 13 wt.-% additive(s).

Unless otherwise indicated, all quantities here relate to the total mass of the materials. The individual quantity ranges can be chosen separately.

Those materials which consist of the named components are particularly preferred. Furthermore, those materials are preferred in which the individual components are in each case selected from the above-named preferred and particularly preferred substances. In addition, materials are particularly preferred which, optionally in addition to the compound of Formula (1), do not contain any volatile mercaptans, i.e. mercaptans which have a typical mercaptan odour. Quite particularly preferred are compositions which do not contain further mercaptans and preferably also do not contain other sulphur compounds. Compositions are further preferred which do not contain other chain regulators in addition to the compounds of Formula 1.

The materials according to the invention are suitable in particular as dental materials, in particular as dental cements, filling composites and veneering materials and as materials for the manufacture of prostheses, artificial teeth, inlays, onlays, crowns and bridges. They have similar mechanical properties (bending strength and elastic modulus) to materials based on dimethacrylates, but are characterized by a reduced polymerization shrinkage stress (PSS), improved impact strength and low intrinsic odour.

The dental materials are suitable primarily for intraoral application by the dentist to restore damaged teeth (clinical materials), i.e. for therapeutic application, e.g. as dental cements, filling composites and veneering materials. However, they can also be used extraorally, for example in the manufacture or repair of dental restorations, such as prostheses, artificial teeth, inlays, onlays, crowns and bridges (technical materials).

A further subject-matter of the invention are homo- and copolymers which could be obtained by polymerization of dental materials according to the invention. Polymers of this type can be processed to form prostheses or artificial teeth, for example by machining processes. They are preferably available in the form of cylindrical or disk-shaped blanks.

The materials according to the invention are suitable in addition for the manufacture of mouldings which can be manufactured e.g. by casting, compression moulding or 3D printing. The improved impact strength in particular allows these materials to come to the same level as common thermoplastics. In addition, the small delay in curing is essential for 3D printing.

In addition, the invention relates to the use of compounds of Formula 1 as chain transfer agents in the radical polymerization or to regulate or control the network structure in the polymerization in particular of (meth)acrylates.

EXAMPLES

Example 1

Synthesis of 2-methanesulphonyloxyacrylic Acid Ethyl Ester (1)

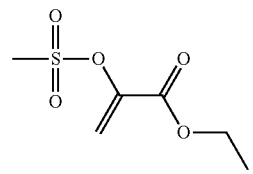

Triethylamine (TEA, 24.23 g, 0.24 mol) was added to a solution of pyruvic acid ethyl ester (23.22 g, 0.20 mol) in dichloromethane (200 ml) at −5° C. Methanesulphonyl chloride (27.49 g, 0.24 mol) was added dropwise. The reaction mixture was then stirred further first of all for 1 h at −5° C. and then at ambient temperature. After 22 h, the yellow reaction solution was washed with water (5×100 ml) and saturated aqueous NaCl solution (100 ml), dried over anhydrous $Na_2SO_4$, filtered and concentrated on a rotary evaporator. The crude product was purified by means of column chromatography ($SiO_2$, n-hexane/ethyl acetate 9:1). 14.99 g (39% yield) of a yellowish liquid was obtained.

$^1$H-NMR (CDCl$_3$, 400 MHz): δ=1.35 (t, 3H; J=7.2 Hz; CH$_3$), 3.28 (s, 3H; S—CH$_3$), 4.31 (q, 2H; J=7.2 Hz; O—CH$_2$), 5.81 (d, 1H; J=2.3 Hz; =CH), 6.22 (d, 1H; J=2.3 Hz; =CH).

$^{13}$C-NMR (CDCl$_3$, 100.6 MHz): δ=13.9 (CH$_3$), 38.8 (S—CH$_3$), 62.2 (O—CH$_2$), 117.4 (=CH$_2$), 142.9 (=C), 161.0 (C=O).

IR (neat): 2986 (w), 2942 (w), 1731 (s), 1638 (m), 1468 (w), 1362 (s), 1334 (m), 1296 (s), 1187 (s), 1172 (m), 1136 (vs), 1019 (m), 956 (s), 895 (m), 861 (m), 790 (s), 684 (m), 627 (m) cm$^{-1}$.

Elemental analysis: Calc. for $C_6H_{10}O_5S$: C, 37.11; H, 5.19; S, 16.51. Found: C, 37.31; H, 5.18; S, 16.40.

Example 2

Synthesis of 2-(toluene-4-sulphonyloxy)-acrylic Acid Ethyl Ester (2)

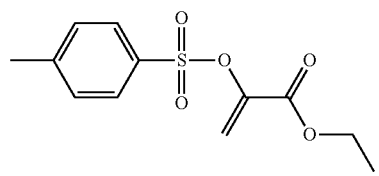

TEA (9.11 g, 90.0 mmol) was added dropwise to a solution of pyruvic acid ethyl ester (5.81 g, 50.0 mmol), p-toluene-sulphonyl chloride (11.44 g, 60.0 mmol) and N,N-dimethylaminopyridine (DMAP, 0.44 g, 3.6 mmol) in dichloromethane (100 ml). The reaction solution was stirred for 24 h at ambient temperature, washed with water (3×100 ml) and saturated aqueous NaCl solution (100 ml), dried over anhydrous $Na_2SO_4$, filtered and concentrated on a rotary evaporator. The crude product was purified by means of column chromatography ($SiO_2$, n-hexane/ethyl acetate 9:1). 8.88 g (66% yield) of a yellowish oil was obtained.

$^1$H-NMR ($CDCl_3$, 400 MHz): δ=1.22 (t, 3H; J=7.2 Hz; $CH_3$), 2.45 (s, 3H; Ar—$CH_3$), 4.15 (q, 2H; J=7.2 Hz; O—$CH_2$), 5.62 (d, 1H; J=2.1 Hz; =CH), 6.14 (d, 1H; J=2.4 Hz; =CH), 7.36 (d, 2H; J=8.2 Hz; Ar—H), 7.83 (d, 2H; J=8.4 Hz; Ar—H).

$^{13}$C-NMR ($CDCl_3$, 100.6 MHz): δ=13.8 ($CH_3$), 21.5 (Ar—$CH_3$), 61.9 (O—$CH_2$), 116.8 (=$CH_2$), 128.4 (Ar—CH), 129.6 (Ar—CH), 132.4 (Ar—C), 143.2 (=C), 145.5 (Ar—C), 160.7 (C=O).

IR (neat): 2984 (w), 1732 (s), 1639 (m), 1597 (m), 1494 (w), 1447 (w), 1372 (s), 1293 (s), 1194 (s), 1178 (s), 1140 (vs), 1090 (s), 1018 (m), 955 (s), 894 (m), 860 (m), 815 (m), 781 (m), 710 (s), 695 (s), 660 (s) $cm^{-1}$.

Elemental analysis: Calc. for $C_{12}H_{14}O_5S$: C, 53.32; H, 5.22; S, 11.86. Found: C, 53.49; H, 5.23; S, 11.57.

Example 3

Synthesis of triethylene glycolbis[2-(toluene-4-sulphonyloxy)-acrylate] (3)

1$^{st}$ Stage: Triethylene Glycol Dipyruvate

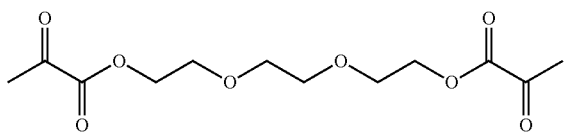 [SMILES: CC(=O)C(=O)OCCOCCOCCOC(=O)C(C)=O]

A solution of pyruvic acid (9.25 g, 0.105 mol), triethylene glycol (7.51 g, 50.0 mmol) and DMAP (0.60 g, 5.0 mmol) in dichloromethane (100 ml) was cooled to −5° C. N,N'-Dicyclohexylcarbodiimide (22.69 g, 0.11 mol) was added slowly. The reaction mixture was stirred further for 2 h at 0° C. and then at rt. After 24 h, the suspension was filtered over a layer of silica gel ($SiO_2$, ethyl acetate). The filtrate was concentrated on a rotary evaporator. The crude product was purified by means of column chromatography ($SiO_2$, n-hexane/ethyl acetate 1:1). 6.08 g (42% yield) of a yellow liquid was obtained.

$^1$H-NMR ($CDCl_3$, 400 MHz): δ=2.48 (s, 6H; $CH_3$), 3.67 (s, 4H; $CH_2$), 3.80 (m, 4H; $CH_2$), 4.40 (m, 4H; $CH_2$).

$^{13}$C-NMR, ($CDCl_3$, 100.6 MHz): δ=26.4 ($CH_3$), 65.0 ($CH_2$), 68.2 ($CH_2$), 70.3 ($CH_2$), 160.4 (C=O), 191.3 (C=O).

IR (neat): 3452 (w), 2874 (w), 1727 (vs), 1450 (w), 1420 (w), 1358 (m), 1298 (s), 1123 (s), 1029 (m), 975 (m), 944 (m), 857 (m), 718 (m), 604 (m) $cm^{-1}$.

Elemental analysis: Calc. for $C_{12}H_{18}O_8$: C, 49.65; H, 6.25.

Found: C, 49.16; H, 6.45.

2$^{nd}$ Stage: Triethylene glycolbis[2-(toluene-4-sulphonyloxy)-acrylate] (3)

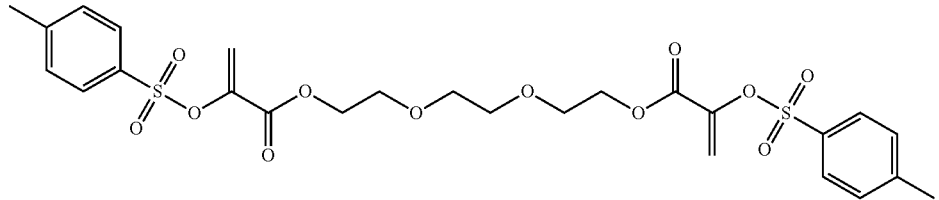

Triethylene glycol dipyruvate (5.81 g, 20.0 mmol), p-toluene-sulphonyl chloride (9.53 g, 50.0 mmol) and N,N-dimethylaminopyridine (0.36 g, 3.0 mmol) were dissolved in dichloromethane (100 ml) and triethylamine (7.29 g, 72.0 mmol) was added dropwise. The reaction mixture was stirred for 24 h at rt, washed with water (3×100 ml) and saturated aqueous NaCl solution (100 ml), dried over $Na_2SO_4$, filtered and concentrated on a rotary evaporator. The brown oil was dissolved in n-hexane/ethyl acetate 1:1 (25 ml) and dichloromethane (5 ml) and filtered over a layer of silica gel ($SiO_2$, n-hexane/ethyl acetate 1:1). The filtrate was concentrated on a rotary evaporator. Diethyl ether (100 ml) was added to the brownish oil. A brownish precipitate was formed. This was filtered off, further purified by repeated digestion with diethyl ether and dried in a vacuum drying oven. 3.64 g (30% yield) of a white solid was obtained (mp: 94° C.).

$^1$H-NMR ($CDCl_3$, 400 MHz): δ=2.45 (s, 6H; Ar—$CH_3$), 3.65 (s, 4H; $CH_2$), 3.68 (m, 4H; $CH_2$), 4.26 (m, 4H; $CH_2$), 5.60 (d, 2H; J=2.2 Hz; =CH), 6.15 (d, 2H; J=2.2 Hz; =CH), 7.36 (d, 4H; J=8.1 Hz; Ar—H), 7.84 (d, 4H; J=8.2 Hz; Ar—H).

$^{13}$C-NMR ($CDCl_3$, 100.6 MHz): δ=21.6 ($CH_3$), 64.9 ($CH_2$), 68.5 ($CH_2$), 70.5 ($CH_2$), 117.1 (=$CH_2$), 128.5 (Ar—CH), 129.7 (Ar—CH), 132.3 (Ar—C), 142.9 (=C), 145.6 (Ar—C), 160.8 (C=O).

IR (neat): 3053 (w), 2958 (w), 2911 (w), 2865 (w), 1735 (s), 1636 (m), 1596 (m), 1495 (w), 1460 (m), 1372 (s), 1328 (w), 1301 (m), 1250 (w), 1192 (s), 1177 (s), 1147 (s), 1130 (vs), 1088 (s), 1051 (m), 1017 (m), 958 (m), 906 (w), 875 (m), 850 (m), 823 (m), 806 (m), 798 (m), 784 (s), 713 (s), 693 (s), 658 (s), 638 (m) $cm^{-1}$.

Elemental analysis: Calc. for $C_{26}H_{30}O_{12}S_2$: C, 52.17; H, 5.05; S, 10.71. Found: C, 51.93; H, 5.45; S, 10.70.

Example 4

Synthesis of 2-(toluene-4-sulphonylmethyl)-acrylic Acid Ethyl Ester (4) (Comparison Example)

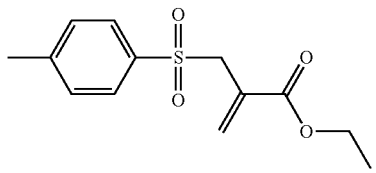 [SMILES: C=C(CS(=O)(=O)c1ccc(C)cc1)C(=O)OCC]

Ethyl 2-(bromomethyl)acrylate (1.13 g, 5.8 mmol), sodium p-toluenesulphinate (1.15 g, 6.4 mmol) and 0.12 g polyethylene oxide 400 were placed in 10 ml absolute THF under an argon atmosphere. Heating then took place for 5 hours at reflux, wherein the reaction progress was monitored by means of NMR spectroscopy and thin-layer chromatography. Once the reaction was complete, the reaction solution was diluted with 10 ml deionized water and 10 ml diethyl ether. The aqueous phase was extracted three times, with 25 ml diethyl ether in each case. The combined organic phases were then washed with brine, dried over sodium sulphate and solvents were removed with a rotary evaporator. The crude product obtained was purified using column chromatography with a mixture of PE/EE 2/1. ($R_f$=0.53). Yield 86%.

$^1$H-NMR (200 MHz, CDCl$_3$, δ): 1.17 (t, J=7.2 Hz, 3H; —COO—CH$_2$—$\underline{CH_3}$), 2.43 (s, 3H; Ar—CH$_3$), 4.02 (q, J=7.2 Hz, 2H; —COO—$\underline{CH_2}$—CH$_3$), 4.13 (s, 2H; —SO$_2$—$\underline{CH_2}$—C—), 5.89 (s, 1H; =CH$_2$), 6.49 (s, 1H; =CH$_2$), 7.32 (d, J=8.2 Hz, 2H; Ar—H), 7.73 (d, J=8.2 Hz, 2H; Ar—H).

$^{13}$C-NMR (50 MHz, CDCL$_3$, δ): 14.0 (C1), 21.6 (C1), 57.5 (C2), 61.4 (C2), 128.8 (C3), 129.2 (C4), 129.6 (C3), 133.2 (C2), 135.4 (C4), 144.8 (C4), 164.8 (C=O).

Example 5

Synthesis of Triethylene glycolbis[2-methane sulphonyloxy)acrylate] (5)

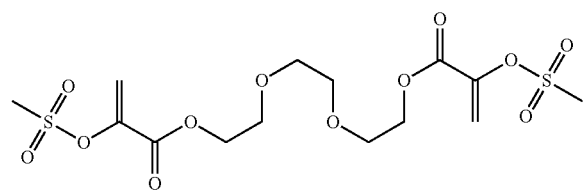

Triethylamine (15.69 g, 0.155 mol) was added to a solution of triethylene glycol dipyruvate (5.19 g, 17.9 mmol) in dichloromethane (100 ml) at −5° C. Methanesulphonyl chloride (17.76 g, 0.155 mol) was added dropwise. The reaction mixture was then stirred further first of all for 1 h at −5° C. and then at ambient temperature. After 24 h, the yellow-brown reaction solution was washed with water (5×100 ml) and saturated aqueous NaCl solution (100 ml), dried over Na$_2$SO$_4$, filtered and concentrated on a rotary evaporator. The crude product was purified by means of column chromatography (SiO$_2$, n-hexane/acetone 3:2; R$_F$=0.22). 1.69 g (3.8 mmol; 21%) of a yellowish liquid was obtained.

$^1$H-NMR (CDCl$_3$, 400 MHz): δ=3.28 (s, 6H; CH$_3$), 3.65 (s, 4H; CH$_2$), 3.75 (m, 4H; CH$_2$), 4.39 (m, 4H; CH$_2$), 5.83 (d, 2H; J=2.4 Hz; =CH), 6.26 (d, 2H; J=2.4 Hz; =CH).

$^{13}$C-NMR (CDCl$_3$, 100.6 MHz): δ=38.9 (CH$_3$), 65.1 (CH$_2$), 68.7 (CH$_2$), 70.5 (CH$_2$), 118.2 (=CH$_2$), 142.7 (=C), 161.1 (C=O).

IR (neat): 3025 (w), 2940 (w), 1732 (s), 1638 (m), 1454 (w), 1358 (s), 1294 (s), 1185 (s), 1135 (vs), 1031 (m), 954 (vs), 863 (m), 789 (s), 686 (s), 628 (m) cm$^{-1}$.

Example 6

Synthesis of diethyl-2,2'-([1,3-phenyldisulphonyl]bis[oxy])diacrylate 6

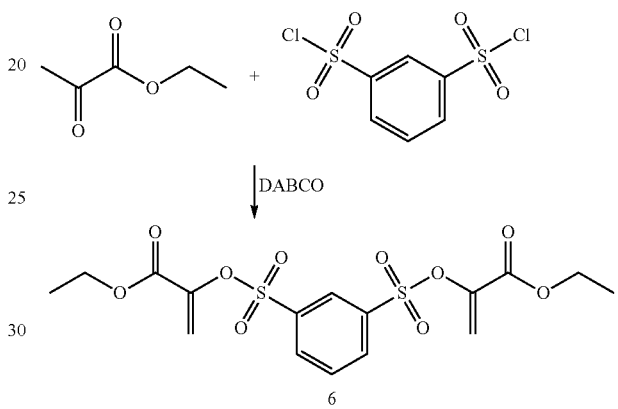

A solution of ethyl pyruvate (9.70 g, 83.5 mmol) and benzenedisulphonyl chloride (10.66 g, 116.3 mmol) in absolute CH$_2$Cl$_2$. (150 ml) was added dropwise to a solution of 1,4-diazabicyclo[2.2.2]octane (13.05 g, 38.8 mmol) in absolute CH_Cl$_2$ (50 ml), accompanied by stirring and in argon atmosphere. The reaction solution was stirred for 72 h at room temperature, diluted with CH$_2$Cl$_2$ (200 ml) and filtered through silica gel. The working-up was carried out by solvent extraction with 1% strength HCl (2×150 ml), deionized water (2×150 ml) and saturated aqueous NaCl solution (150 ml). The organic phase was dried over anhydrous Na$_2$SO$_4$, filtered and concentrated on a rotary evaporator, wherein 12.38 g (73% theoretical) of (6) was obtained as a slightly viscous, yellowish liquid with an NMPR purity of 98%. Rf: 0.50 (PE/EE 2:1)

$^1$H-NMR (CDCl$_3$, 200 MHz): δ=8.46 (t, 1H, J=1.47 Hz, ar-2H), 8.21 (t, 2H, J=7.33 Hz, ar-4H, ar-6H) 7.77 (t, 1H, J=7.93, ar-5H), 6.16 (d, 2H, J=2.49 Hz, 2x >C=CH$_2$, cis), 5.69 (d, 2H, J=2.54 Hz, 2x >C=CH$_2$, trans), 4.09 (q, 4H, J=6.79 Hz, 2x O—CH$_2$—), 1.17 (t, 6H, J=7.14 Hz, 2x —CH$_3$).

$^{13}$C-NMR (CDCl$_3$, 50 MHz, 6): 181.9 (>C=), 160.4 (O—C=O), 143.0 (ar-S), 133.9 (ar-C4, ar-C6), 133.7 (ar-C5), 134.4 (ar-C2), 117.8 (=CH$_2$), 62.2 (O—CH$_2$—), 13.8 (—CH$_3$).

Example 7

Reactivity Measurements

In order to compare the reactivity of the compounds of Formula 1 with known concepts, photo-DSC measurements were carried out with the mixtures prepared. An equimolar mixture of the commercially available dimethacrylate urethane dimethacrylate (UDMA, isomer mixture; CAS: 72869-86-4) and 1,10-decanediol dimethacrylate (D₃MA) (resin mixture 2M) was used as unmodified base resin in order to obtain cross-linked polymers. 0.20 double-bond equivalents of the respective regulator of Formula 1 was then added to this base mixture. In the case of compounds with insufficient solubility, the proportion was reduced to 0.05 double-bond equivalents (indicated in Table 4 with *).

A Netzsch DSC 204 F1 with autosampler was used for the polymerization. The measurement was carried out isothermally at 25° C. under a nitrogen atmosphere. 10±1 mg of the sample mixture was weighed into an aluminium DSC crucible which was placed into the DSC chamber by means of the autosampler. The sample was rinsed for 4 min with nitrogen (20 ml/min) and then irradiated for 5 min by means of filtered UV light (400-500 nm; Omnicure 2000) with an intensity of 1 W/cm² at the beam outlet of the lamp. The time to achieve 95% of the maximum conversion ($t_{95}$) and the time to achieve the maximum polymerization rate ($t_{max}$) were used to assess the reactivity.

Since, besides the polymerization rate, it is also essential to regulate the molecular weight, in addition samples were prepared with monofunctional benzyl methacrylate (BMA). The samples were likewise rinsed for 4 min with nitrogen (20 ml/min) and then irradiated for 5 min by means of filtered UV light (400-500 nm; Omnicure 2000) with an intensity of 1 W/cm² at the beam outlet of the lamp. The polymerized samples were dissolved in THF and analyzed with a Waters GPC with three columns (Styragel HR 0.5, Styragel HR 3 and Styragel HR 4) connected in series and a Waters 2410 RI detector in a column oven at 40° C. and with a flow rate of 1.0 ml/min. Polystyrene standards were used for calibration. The ratio between the number average molecular weight of the modified polymer and that of pure poly-BMA ($Mn_{mod}/Mn_{BMA}$) shows how markedly the average molecular weight is reduced by the regulator. What is desirable is a marked reduction in the molecular weight, i.e. a low value of the ratio $Mn_{mod}/Mn_{BMA}$, at the same time as a high polymerization rate, i.e. relatively low values for $t_{95}$ and $t_{max}$ in the above reaction with UDMA/D₃MA. In addition, it is desirable to achieve a high double bond conversion (DBC) in order to ensure the necessary mechanical properties of the polymer. In the following, the double bond conversion for the monomer mixture UDMA/D₃MA is denoted as $DBC_{U/D}$ and that for the BMA monomer alone is denoted with $DBC_{BMA}$.

Compounds 1 and 2 according to the present invention were compared with other compounds as regulators.

Comparison example V1 is either the pure methacrylate-based mixture of equal parts by weight of UDMA and D₃MA or the monofunctional methacrylate BMA. Comparison example V2 is composed of a mixture of V1 and the β-allyl sulphone 4 (Example 4), which was used as the analogue to compound 2. V3 to V12 are comparison examples of methacrylates (either based on UDMA/D₃MA or BMA) with the most varied known regulators which differ on the basis of their leaving group (sulphone, sulphide, phosphone, alkyl) or activation group (ester, amide, aromatic). V13 is a formulation with a Barton ester as regulator.

TABLE 1

| Regulator | Ex. | $t_{95}$ [s] | $t_{max}$ [s] | $Mn_{mod}/Mn_{BMA}$ [ ] | $DBC_{U/D}/DBC_{BMA}$ [%] / / [%] |
|---|---|---|---|---|---|
| none (UDMA/D₃MA or BMA) | V1 | 66.4 | 4.3 | — | 74 / / — |
| 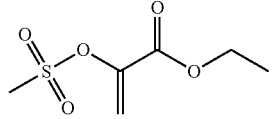 1 | 1 | 65.6 | 15.3 | 0.30 | 94 / / 55 |
| 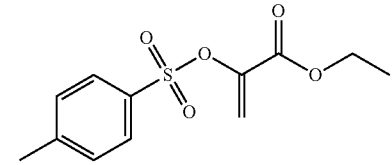 2 | 2 | 55.6 | 12.1 | 0.12 | 93 / / 57 |
| 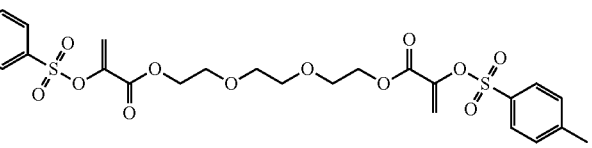 3 | 3 | 65.0 | 7.5 | 0.32 | 95 / / 56 |
| 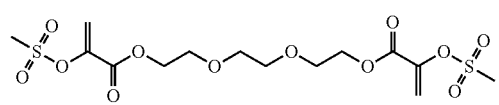 5 | 5 | 65.0 | 9.2 | 0.30 | 97 / / 55 |

TABLE 1-continued
| Regulator | Ex. | $t_{95}$ [s] | $t_{max}$ [s] | $Mn_{mod}/Mn_{BMA}$ [ ] | $DBC_{U/D}//DBC_{BMA}$ [%] // [%] |
|---|---|---|---|---|---|
| 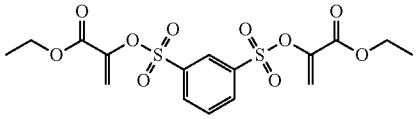<br>6 | 6 | 44.3 | 7.8 | 0.22 | 93 // 82 |
| 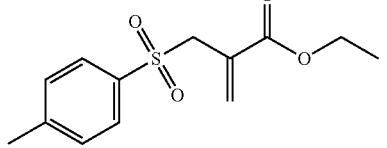<br>4 | V2 | 82.6 | 10.2 | 0.18 | 61 // 46 |
| 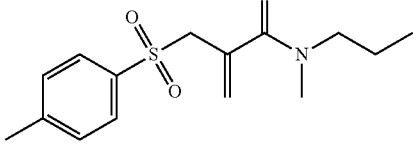 | V3 | 33.2 | 5.1 | 1.16 | 86 // 76 |
| 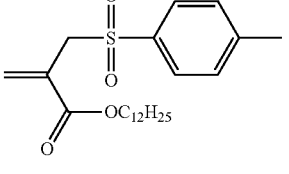 | V4 | 114.3 | 4.1 | 0.20 | 70 // 52 |
| 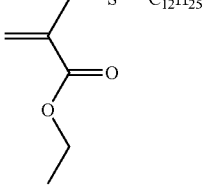 | V5 | 108 | 10.7 | 0.22 | 63 // 36 |
| 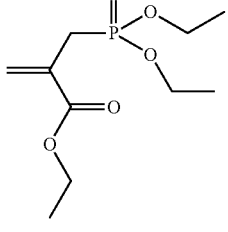 | V6 | 181.2 | 12 | 0.53 | 49 // 17 |
|  | V7 | 73 | 16.1 | 0.47 | — // 21 |
| 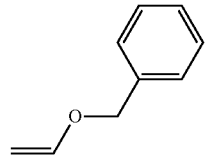 | V8 | 73.2 | 8.1 | 0.66 | — // 16 |
| 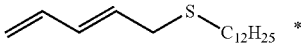 * | V9 | 117.8 | 12.3 | 0.40 | — // 13 |

TABLE 1-continued

| Regulator | Ex. | $t_{95}$ [s] | $t_{max}$ [s] | $Mn_{mod}/Mn_{BMA}$ [ ] | $DBC_{UD}//DBC_{BMA}$ [%] // [%] |
|---|---|---|---|---|---|
| (diethyl (2-phenylallyl)phosphonate structure) | V10 | 107.8 | 9.9 | 0.49 | — // 15 |
| (4-methyl-3-(benzoyloxy)thiazole-2(3H)-thione structure) * | V11 | 74.5 | 11 | 0.45 | 75 // 46 |
| (2-((4-methylphenyl)sulfonylmethyl)acrylonitrile structure) * | V12 | 102.1 | 7.8 | 0.51 | 57 // 33 |
| (((2-phenylallyl)sulfonyl)-4-methylbenzene structure) * | V13 | 74 | 11.3 | 0.43 | 64 // 26 |

* low solubility, therefore c = 5 DB %
V Comparison example

From Table 1 above it can be clearly seen that compounds 1, 2, 3, 5 and 6 when used according to the invention as regulator were surprisingly in the position to shorten the time $t_{95}$ until 95% conversion was achieved, which in the comparison examples was only possible with the compound from comparison example V3, an allyl sulphone. However, this compound actually increased the average molecular weight of the obtained polymer by 16%, instead of reducing the chain length. In contrast thereto, the compounds according to the present invention effected a significant reduction to up to approximately ⅛ of the unmodified product. At the same time, however, they effected an increase in the time tx until the maximum polymerization rate was achieved, sometimes by up to 3 or 4 times (compounds 1 and 2), which is advantageous since the reaction mixture then gels only much later with the result that the polymerization can proceed uninhibited for longer under substantially homogeneous conditions. Not a single one of the comparison examples exhibited such a desirable combination of properties. Since compound 4 in comparison example V2 known from Moad et al. (see above) performed best in this regard, this was used below for further comparisons with the sulphonic acid esters for the use according to the invention.

Example 8

Preparation and Characterization of Photopolymers with Dimethacrylates and the Transfer Reagents (Regulators) from Examples 1, 2 and 4

Resin formulations were prepared from a 1/1 mixture (mol/mol) of UDMA and $D_3MA$ (resin mixture 2M) and from a mixture of UDMA, $D_3MA$ with transfer reagent 1, 2 or 4 (1/1/1 molar mixture specified in wt.-% transfer reagent). All formulations also contained ~1 wt.-% MBDEGe as photoinitiator. To check the photoreactivity, the formulations prepared were measured using a photorheometer MCR302 WESP from Anton Paar, which was coupled with a Bruker Vertex 80 IR spectrometer to monitor conversion. A PP-25 measuring system was used and the measuring gap was set to 0.1 mm. Before and during curing (1 W/cm$^2$; 400-500 nm; Omnicure 2000), the storage modulus and loss modulus of the sample were measured in the oscillation mode (1% deflection, 10 Hz). At the same time, during the measurement, IR spectra of the sample with a frequency of ~5 Hz were recorded. The achievement of the gel point (intersection of the storage modulus and the loss modulus) and the time until 95% of total conversion ($t_{95\%}$) were used as a measure of the photoreactivity. In addition it was possible to determine the conversion at the gel point ($DBC_9$), the total conversion (DBC) and the photopolymerization-induced shrinkage stress ($F_S$ and $F_S$ at 75% conversion $F_{S(75\%)}$). The results obtained are summarized in Table 2.

TABLE 2

RT NIR Photorheometry

| Formulation | Gel point [s] | $DBC_g$ [%] | DBC [%] | $t_{95\%}$ [s] | $F_{S(75\%)}$ [N] | $F_s$ [N] |
|---|---|---|---|---|---|---|
| 2M[a]* | 2.1 | 41 | 79 | 69.0 | −14.9 | −17.9 |
| 2M + 20 wt.-% 1 | 10.4 | 46 | 95 | 48.2 | −9.9 | −19.5 |
| 2M + 26 wt.-% 2 | 7.9 | 56 | 93 | 25.9 | −8.8 | −15.6 |
| 2M + 26 wt.-% 4* | 12.4 | 38 | 76 | 110.5 | −9.7 | −12.0 |

[a])2M: UDMA/D3MA 1/1
*Comparison example

It can be clearly seen that the conversion at the gel point can be increased by means of transfer reagents 1 and 2 and comparison reagent 4, which results in an increased total conversion and a reduced shrinkage stress. However, in contrast to comparison reagent 4, with transfer reagents 1 and 2 the reaction period ($t_{95\%}$) is barely affected and a significantly greater total conversion is achieved.

Example 9

DMTA Analysis of the Photopolymers Prepared

To determine the glass transition, the formulations prepared in Example 8 were poured into silicone moulds and polymerized in a light furnace (Lumamat 100 model, Ivoclar AG) using program 2 (P2: 10 min irradiation with an intensity of approx. 20 mW/cm²). The rods were turned and cured again using P2. The test rods were ground and then measured on an Anton Paar Rheometer MCR301 with a CTD oven (Convection Temperature Control) and an installed solid-clamping device (SRF12 for rectangular cross-sections up to 12 mm). The heating rate set was 2° C./min. All samples were heated from −100° C. to 200° C. and oscillated at a constant frequency of 1 Hz and 0.1% deflection. The measured values shown in Table 3 show that a lower and significantly narrower glass transition range can be achieved through addition of the transfer reagents 1, 2 and 4.

TABLE 3

DMTA

| Formulation | $G'_{(20°)}$ [MPa] | $T_G$ [° C.] | HW [° C.] | $G'_r$[a] [MPa] |
|---|---|---|---|---|
| 2M[b]*) | 940 | 150 | 146 | 81.9 |
| 2M + 20 wt.-% 1 | 999 | 69 | 23 | 6.0 |
| 2M + 26 wt.-% 2 | 1020 | 68 | 25 | 9.8 |
| 2M + 26 wt.-% 4*) | 810 | 72 | 23 | 4.4 |

[a])Storage modulus on the rubbery-elastic plate
[b])2M: UDMA/D3MA 1/1
*)Comparison example The glass transition temperature (To) can be set and a sharper glass transition range can be obtained (characterized via the half width of the loss factor graph at glass transition, HW) by using transfer reagents 1, 2 and 4. The storage modulus at room temperature ($G'_{(20° C.)}$) remains virtually unchanged and is partly even slightly improved. The effect of compounds 1, 2 and 4 is comparable. Unlike compound 4, however, compounds 1 and 2 according to the invention do not have a delaying effect on the reaction and result in a higher conversion (cf. Ex. 8).

Example 10

Measurement of the Impact Strength (Dynstat Impact Test)

The impact strength properties were determined using the DYNSTAT apparatus in accordance with DIN 53435, wherein the impact strength (impact energy) of unnotched test pieces was determined in the impact bending apparatus. Sample rods (~1×0.45×0.15 cm) were prepared with different formulations and Dynstat impact tests were carried out (using a 5 kpcm hammer; 0.5 J). The values obtained are listed in Table 4 given below.

TABLE 4

Impact strength

| Formulation | Impact energy [kJ/m²][a] |
|---|---|
| 2M[b]* | 2.4 ± 0.4 |
| 2M + 20 wt.-% 1 | 11.3 ± 1.7 |
| 2M + 26 wt.-% 2 | 17.4 ± 1.1 |
| 2M + 26 wt.-% 4* | 6.1 ± 1.75 |

[a])Standardized for width and thickness
[b])2M: UDMA/D3MA 1/1
*Comparison example It can be seen that an increase in impact strength could be achieved with compounds 1, 2 and 4, wherein increases by a factor of 4.7 or 7.25, respectively, were observed with compounds 1 and 2, while comparison compound 4 only effected an increase by a factor of 2.5.

Example 11

Measurement of the Impact Strength (Dynstat Impact Test)

The impact strength properties were determined analogously to Example 10. In Table 5 below the values obtained for formulations with GDVA monomer alone as well as with 24 wt.-% of compound 2 are listed.

TABLE 5

| Formulation | Impact energy [kJ/m²][a] |
|---|---|
| GDVA*) | 5.1 ± 1.0 |
| GDVA + 2 | — |

*)Comparison example
[a])Standardized for width and thickness

Only the samples made of pure GDVA could be broken using this test apparatus, while the test pieces prepared according to the present invention with 24 wt.-% of compound 2 exhibited such high strength that they withstand the impact bending test undamaged.

To interpret this result, the two photopolymers obtained were bent manually. Homopolymers made of GDVA were very brittle and broke relatively easily, in contrast polymers with compound 2 according to the invention could be bent without breaking, as is shown in FIG. 1 for a polymer made of GDVA (on the left) and one made of GDVA and compound 2.

Example 12

Preparation and Characterization of Gels with Polyethylene Glycol Diacrylate

Formulations were prepared with polyethylene glycol diacrylate (PEGDA, Mw ~750 g/mol) alone and with 19 wt.-% of compounds 2 and 4, respectively. All formulations also contained ~0.5 wt.-% Ivocerin as photoinitiator. The resin formulations prepared were mixed with 60 wt.-% dimethyl sulphoxide (DMSO) and, to check the photoreactivity, these formulations were measured analogously to Example 8 using a photorheometer MCR302 WESP from Anton Paar, which was coupled with a Bruker Vertex 80 IR spectrometer to monitor conversion. The results achieved are given in Table 6.

TABLE 6

RT NIR Photorheometry

| Formulation | Gel point [s] | $DBC_g$ [%] | DBC [%] | $F_S$ [N] |
|---|---|---|---|---|
| PEGDA*) | 66 | >99 | >99 | −6.6 |
| PEGDA + 2 | 70 | 88 | >99 | −4.5 |
| PEGDA + 4*) | 205 | 41 | 48 | −0.2 |

*)Comparison example

Like in the photopolymerization of di(meth)acrylates without DMSO, in the homopolymerization of PEGDA there is also a rapid gel formation, which, in an uncontrolled reaction leads to high shrinkage stress (−6.6 N), but also to almost quantitative conversions (>99%). It can be clearly seen that the photopolymerization of acrylate-based DMSO gels is also inhibited by compound 4. The gel point is only achieved very late at >200 s, and the conversion is very low at less than 50%, which also explains the very low shrinkage stress. According to the present invention, the PEGDA polymerization in DMSO can be well regulated with compound 2 and a greatly reduced shrinkage stress is achieved with a constantly high conversion.

The reduced shrinkage stress measured after addition of compound 2 was illustrated in the following way: an optical analysis of the polymerization shrinkage was carried out, for which the DMSO-based PEGDA formulations were poured into a Teflon mould with compound 2 as regulator and irradiated in a Lumamat 100 for 10 min. FIG. 2 shows the thus-obtained gels.

Figure 2A:
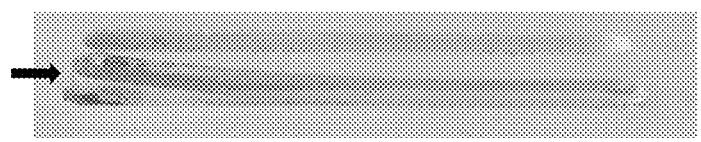
FIGS. 2a and 2b show in each case a photograph of a shrinkage test.
Figure 2B:
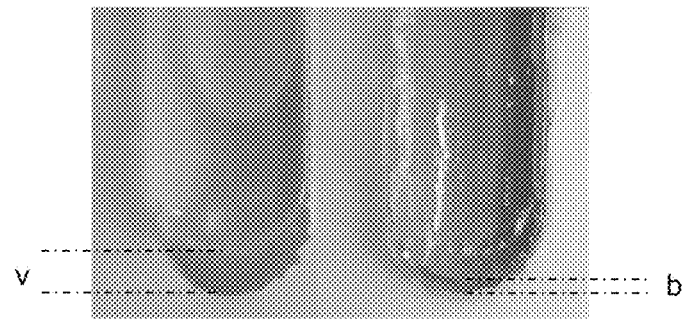

In both photos in FIG. 2 it can be seen that the gel prepared without regulator bends (FIG. 2a, bottom; indicated by the arrow) and the gel prepared with compound 4 contracts greatly in length vis-à-vis that from the comparison example without regulator (FIG. 2b, on the left; difference in length "v"). In contrast, the gel prepared with compound 2 as regulator according to the invention (FIG. 2a, top; FIG. 2b, on the right) hardly shrinks because of the reduced shrinkage stress during the polymerization (difference in length "b").

Example 13

Preparation and Characterization of Coatings with Urethane Diacrylate

Formulations were prepared with the urethane diacrylate (UDA) Ebecryl 2002 from Sartomer alone and with 20 wt.-% of compounds 2 and 4, respectively. All formulations also contained ~1 wt.-% Darocur 1173 (BASF) as photoinitiator. To check the photoreactivity, these formulations were measured analogously to Example 8 using a photorheometer MCR302 WESP from Anton Paar, which was coupled with a Bruker Vertex 80 IR spectrometer to monitor conversion. The results achieved are given in Table 7.

TABLE 7

RT NIR Photorheometry

| Formulation | $t_{95}$ [s] | DBC [%] | $F_S$ [N] |
|---|---|---|---|
| UDA*)*) | 69 | 96 | −7.6 |
| UDA + 2 | 116 | 99 | −0.2 |
| UDA + 4*) | 185 | 73 | −5.2 |

*)Comparison example

From Table 7 it can be seen that the polymer according to the invention was able to increase even further the already high conversion vis-à-vis the product prepared without regulator, but above all exhibited virtually no shrinkage. With compound 4 as regulator, the conversion was significantly lower than without regulator and the shrinkage could only be reduced a little. In addition, compound 4 increased the reaction period substantially compared with compound 2 in the example according to the invention, i.e. by 2.7 times the polymerization without regulator, while in Example 15 it only increased by 1.7 times.

Example 14

Cross-Cut Test of Coatings According to DIN EN ISO 2409

An anodized aluminium foil was coated analogously to the above examples with UDA as monomer and the formulations prepared with 10 or 20 wt.-% of compounds 2 or 4, respectively (4 mil doctor blade, ~102 μm) and cured in a UV oven. The coatings were cut using a cross-cut tester (6×2 mm) and then adhesive tape (Tesafilm Standard 19 mm) was stuck evenly over the cut coatings. The adhesive tapes were pulled off evenly at an angle of ~60° and the appearance of the remaining grid was assessed. Table 8 shows the results achieved.

TABLE 8

Cross-cut test

| Formulation | ISO Rating |
|---|---|
| UDA | GT 3 |
| UDA + 10 wt.-% 2 | GT 1 |
| UDA + 20 wt.-% 2 | GT 1 |
| UDA + 10 wt.-% 4*) | GT 1 |
| UDA + 20 wt.-% 4*) | GT 1 |

*)Comparison example

The UDA-based coating without regulator exhibited a number of flaking squares, whereas with all of the coatings prepared with regulator—both with 10 wt.-% and with 20 wt.-% regulator—only small chips of the coating were flaked off at the intersections and cut edges of the grid lines. In this respect, compounds 2 and 4 had an equal effect as regulator.

Example 15

3D Printing

Reaction mixtures based on an aliphatic polyester urethane methacrylate (Bomar XR 741) with 1 wt.-% Ivocerin® as photoinitiator were prepared for 3D printing. 5, 7 or 10 wt.-%, respectively of compound 2 were mixed in as regulator. According to instructions in the literature (Liska et al., J. Polym. Sci. A Polym. Chem. 49, 4927-4934 (2011)) test rods of type 5B according to DIN EN ISO 527-2 were then pressed and tensile tests were carried out on a Zwick 500 tensile testing machine. The results indicated in Table 9 represent in each case average values from at least 6 measurements.

TABLE 9

Elongation at break of 3D prints

| Formulation | Elongation at break [%] |
|---|---|
| Reaction mixture without regulator*) | 5.01 |
| Reaction mixture + 5% wt.-% 2 | 7.12 |
| Reaction mixture + 7% wt.-% 2 | 8.78 |
| Reaction mixture + 9% wt.-% 2 | 12.32 |

*)Comparison example

It can be clearly seen that the elongation at break is improved by the addition according to the invention of regulator 2.

Example 16

Surface Analyses

Monomer mixtures (resin mixture 2M) were prepared analogously to Example 8 without regulator as well as with 20 wt.-% of compound 1 or 26 wt.-% of compound 2. To determine the micrographs, the formulations prepared were poured into silicone moulds and polymerized in a light furnace (Lumamat 100 model, Ivoclar AG) using program 2 (P2: 10 min irradiation with an intensity of approx. 20 mW/cm$^2$). The rods (~1×0.45×0.15 cm) were turned and again cured according to P2. The test rods were ground and then tested by means of a DYNSTAT apparatus in accordance with DIN 53435, wherein the test pieces were unnotched, using a 5 kpcm hammer analogously to Example 10. The fracture surfaces were then analyzed by means of SEM on an SEM XL-30 from Philips. For this, the samples were fixed to a specimen holder with tape and the edges were coated with a conductive silver solution. The samples were then sputtered with a thin conductive gold layer. Images were taken of the fracture surfaces at 500 times magnification.

Figure 3:
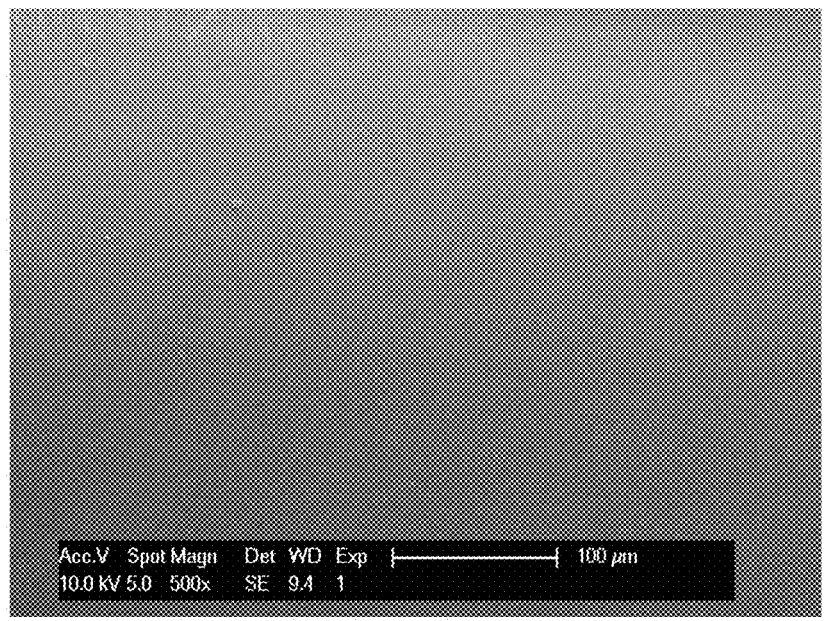
FIGS. 3, 4a and 4b show in each case a photograph of the fracture surface of a polymer.

FIG. 3 shows the fracture surface of the polymer, which had been prepared without the addition of regulator: an extremely smooth fracture surface, which thus displays a brittle fracture.

Figure 4A:
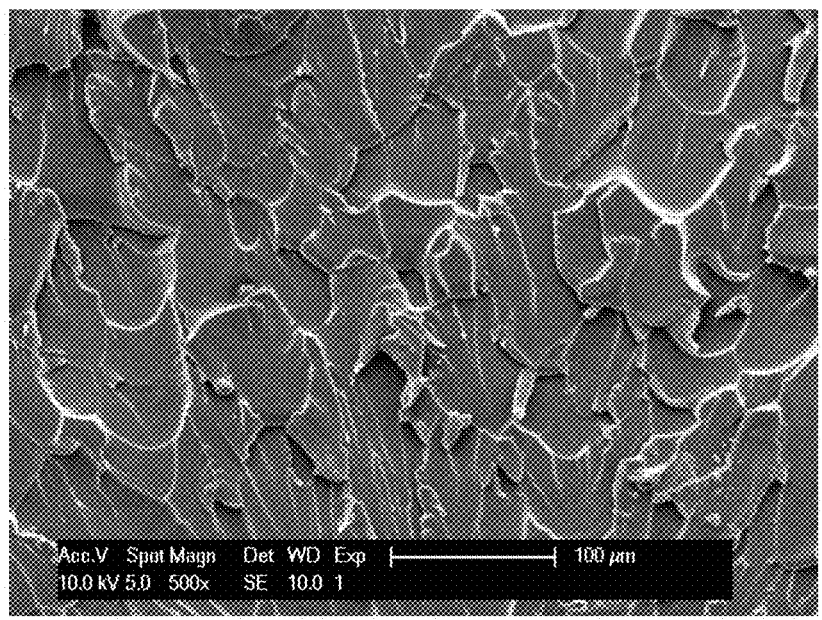
Figure 4B:
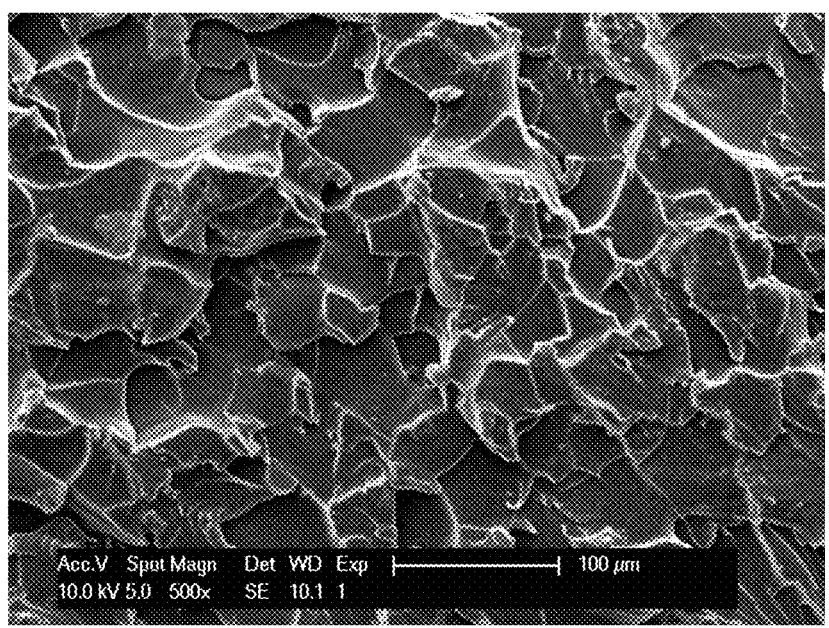

In FIG. 4, the fracture surfaces of the polymer according to the invention with 20 wt.-% (FIG. 4a) or 26 wt.-% of compound 2 (FIG. 4b) are to be seen, which are substantially more ductile than the unregulated dimethacrylate network.

Example 17

Determination of Molecular Weight

Polymers were prepared analogously to Example 8 with benzyl methacrylate (BMA) without regulator as well as with 22 wt.-% compound 1, 28 wt.-% compound 2 and 28 wt.-% compound 4, dissolved in THF and analyzed with a Waters GPC with three columns (Styragel HR 0.5, Styragel HR 3 and Styragel HR 4) connected in series and a Waters 2410 RI detector in a column oven at 40° C. and with a flow rate of 1.0 ml/min using polystyrene standards, wherein the molecular weight (in kDa) and the polydispersity index (PDI) were determined. The results are given in Table 10.

TABLE 10

Determination of molecular weight

| Example | Mn [kDa] | PDI [ ] |
|---|---|---|
| BMA*) | 7.0 | 2.2 |
| BMA + 1 | 1.4 | 1.3 |
| BMA + 2 | 1.1 | 1.3 |
| BMA + 4*) | 1.3 | 1.3 |

*)Comparison example

The values obtained, which correlate well with those from Table 1, show that the polymerization under addition of the three regulators led to significantly shorter chains than in the case of the unregulated reaction. Moreover, as expected, the molecular weight distribution after the addition of regulator also proved to be considerably more uniform. In this example, compound 2 proved to be the most effective of the three regulators tested.

Example 18

Formulation for the 3D Printing

| Component | Type | Quantity (parts by weight) |
|---|---|---|
| Monomer | Dimethacrylates, e.g. polyester urethane dimethacrylate Bomar XR 741 | 100 |
| Regulator | Compound 6 | 12 |
| Initiator | Photoinitiator, such as a bisacylgermanium compound, e.g. Ivocerin | 1 |
| Additives | UV absorbers, e.g. Sudan Yellow | 0.2 |

A particularly good storage stability is achieved through the use of urethane methacrylates. The long-wave absorption of the photoinitiator is matched to the emission spectrum of the 3D printer. The UV absorber prevents scattered light and controls the layer thickness of the curing. The impact strength of the material can be significantly improved by the use according to the invention of the regulator.

Example 19

Formulation for Casting Resins

| Component | Type | Quantity (parts by weight) |
|---|---|---|
| Monomers | Methacrylates, e.g. methyl methacrylate | 75 |
| Regulator | Formula 1 or 2, n = 1, e.g. compound 2 | 20 |
| Fillers | Polymethyl methacrylate (MG 4.76 × 10$^6$) | 4 |
| Initiator | Thermal initiator, e.g. AIBN | 1 |
| Additives | Mould release agent: Stearic acid | 0.005 |

Particularly light-stable, thermally curable casting compounds are obtained through the use of methacrylates. The use of relatively large amounts of the regulator displaces the gel point towards high conversions, whereby the internal stresses in the material can be significantly reduced.

The invention claimed is:

1. Radically polymerizable dental material, which comprises at least one multifunctional (meth)acrylate or a mixture of mono- and multi-functional (meth)acrylates, at least one initiator for the radical polymerization and at least one sulphonic acid ester of Formula 1:

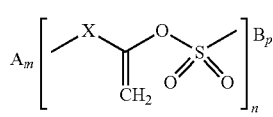

in which the variables have the following meanings:

A H, CN, a cycloaliphatic, linear or branched aliphatic $C_1$-$C_{30}$-hydrocarbon radical, which can be substituted by one or more substituents, which can be interrupted by one or more urethane groups, ester groups, O and/or S and which can contain 1 to 4 benzene groups,
an aromatic $C_6$-$C_{30}$-hydrocarbon radical, which can be substituted by one or more substituents,
or a combination thereof;

X —COO—, —CON($R^1$)— or is absent, wherein the bond to A takes place via O or N;

B a cycloaliphatic, linear or branched aliphatic $C_1$-$C_{30}$-hydrocarbon radical, which can be substituted by one or more substituents, which can be interrupted by one or more urethane groups, ester groups, O and/or S and which can contain 1 to 4 benzene groups,
an aromatic $C_6$-$C_{30}$-hydrocarbon radical, which can be substituted by one or more substituents, tosyl,
or a combination thereof;

$R^1$ hydrogen, a cycloaliphatic, linear or branched aliphatic $C_1$-$C_{10}$-hydrocarbon radical, which can be interrupted by one or more oxygen atoms and which can be substituted by one or more OH groups, or
an aromatic $C_6$-$C_{10}$-hydrocarbon radical, which can be substituted by one or more OH groups;

m an integer from 1 to 6;
n an integer from 1 to 6;
p an integer from 1 to 6; wherein
m and p cannot simultaneously be greater than 1 and wherein, if m=1, p=n, and if p=1, m=n.

2. Dental material according to claim 1 in which the sulphonic acid ester is a compound of Formula 2,

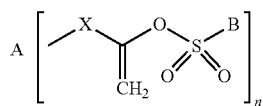

in which the variables have the following meanings:

A H, CN, an aliphatic, linear or branched $C_1$-$C_{30}$-hydrocarbon radical, which can be substituted by one or more substituents, which are selected from $CH_3$, —$C_2H_5$, —OH, —$OCH_3$ and/or —O—$COCH_3$, which can be interrupted by one or more urethane groups, ester groups, O and/or S and which can contain 1 to 4 benzene groups,
which can be substituted by one or more substituents, which are selected from $CH_3$, —$C_2H_5$, —OH, —$OCH_3$ and/or —O—$COCH_3$,
or a combination thereof;

X —COO—, —CON($R^1$)— or is absent, wherein the bond to A takes place via O or N and wherein X is absent, if A is an aromatic hydrocarbon radical or CN;

B an aliphatic, linear or branched $C_1$-$C_{20}$-hydrocarbon radical, which can be substituted by one or more, substituents, which can be interrupted by one or more, urethane groups, ester groups, O or S and which can contain 1 to 4 benzene groups,
an aromatic $C_6$-$C_{18}$-hydrocarbon radical, which can be substituted by one or more, substituents;

$R^1$ hydrogen or a linear or branched aliphatic $C_1$-$C_{10}$-hydrocarbon radical, which can be interrupted by one or more, oxygen atoms and which can be substituted by one or more OH groups;

n an integer from 1 to 6.

3. Dental material according to claim 2, in which the variables of Formula 2 have the following meanings:

A an aliphatic linear or branched $C_1$-$C_{20}$-hydrocarbon radical, which can be interrupted by one or more 1,4-phenylene groups, urethane groups, ester groups, O and/or S and which can be substituted by one or more OH groups, or a phenyl radical, which can be substituted by one or more substituents;

X —O—CO— or is absent, wherein the bond to A takes place via O and wherein X is absent if A is an aromatic hydrocarbon radical or CN;

B an aliphatic linear or branched $C_1$-$C_{20}$-hydrocarbon radical, which can be interrupted by one or more oxygen atoms and which can contain 1 to 4 benzene groups which can be substituted by 1 or 2 —$OCH_3$ or —$CH_3$ group(s);

n 1 or 2.

4. Dental material according to claim 1 in which the sulphonic acid ester is a compound of Formula 3,

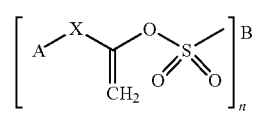

in which the variables have the following meanings:

A hydrogen, —CN, a phenyl radical, which can be substituted by one or more substituents, which can be interrupted by one or more urethane groups, ester groups, O and/or S, which can contain 1 to 4 benzene groups, and which can be substituted by one or more OH groups;

B a cycloaliphatic, linear or branched aliphatic $C_1$-$C_{20}$-hydrocarbon radical, which can be substituted by one or more OH groups, which can be interrupted by one or more urethane groups, ester groups, O and/or S and which can contain 1 to 4 benzene groups,
an aromatic $C_6$-$C_{18}$-hydrocarbon radical, which can be substituted by one or more OH groups,
or a combination thereof;

X —COO— or —CON($R^1$)— or is absent, wherein the bond to A takes place via O or N and wherein X is absent, if A is an aromatic hydrocarbon radical or CN;

$R^1$ hydrogen or a linear or branched aliphatic $C_1$-$C_{10}$-hydrocarbon radical, which can be interrupted by one or more oxygen atoms and which can be substituted by one or more OH groups;

n an integer from 2 to 4.

5. Dental material according to claim 4, in which the variables of Formula 3 have the following meanings:

A H, a phenyl radical, which can be substituted by one or more substituents comprising —CH$_3$, —OH, —OCH$_3$, or an aliphatic, linear or branched C$_1$-C$_8$-hydrocarbon radical, which can be interrupted by one or more urethane groups, ester groups and/or O;

B an aliphatic, linear or branched C$_1$-C$_{10}$-hydrocarbon radical, which can be interrupted by one or more O atoms and which can contain 1 to 4 benzene groups, an aromatic C$_6$-C$_{10}$-hydrocarbon radical, or a combination thereof;

X —COO— or is absent, wherein the bond to A takes place via O and wherein X is absent, if A is an aromatic hydrocarbon radical or CN; and n 2.

6. Dental material according to claim 1, which comprises at least one filler.

7. Dental material according to claim 1, which comprises
(a) 0.5 to 40 wt.-% of at least one compound of general formula 1,
(b) 0.01 to 5.0 wt.-% initiator(s) for the radical polymerization, and optionally
(c) 5 to 80 wt.-% multifunctional (meth)acrylate (s),
in each case relative to the total mass of the dental material.

8. Dental material according to claim 7 for use as prosthesis material, adhesive or coating material which comprises
(a) 0.5 to 40 wt.-% of at least one compound of general formula 1,
(b) 0.01 to 5.0 wt.-% initiator(s),
(c) 5 to 80 wt.-% wt.-% multifunctional (meth) acrylate (s),
(d) 0 to 40 wt.-% monofunctional (meth)acrylate (s),
(e) 0 to 5 wt.-% additive(s),
(f) 0 to 60 wt.-%
in each case relative to the total mass of the dental material.

9. Dental material according to claim 7 for use as composite, filling composite or cement, which comprises
(a) 0.5 to 30 wt.-% of at least one compound of general formula 1,
(b) 0.01 to 5.0 wt.-% initiator(s),
(c) 5 to 50 wt.-% multifunctional (meth)acrylate(s),
(d) 0 to 30 wt.-% monofunctional (meth)acrylate(s),
(e) 5 to 85 wt.-% filler(s), and
(f) 0 to 5 wt.-% additive(s),
in each case relative to the total mass of the dental material.

10. Dental material according to claim 1 for intraoral use to restore damaged teeth.

11. Dental material according to claim 1 in which the variables have the following meanings:

A H, CN, an aliphatic, linear or branched C$_1$-C$_{30}$-hydrocarbon radical, which can be substituted by 1 to 4, substituents, which are selected from CH$_3$, —C$_2$H$_5$, —OH, —OCH$_3$ and/or —O—COCH$_3$, which can be interrupted by 1 to 4 urethane groups, ester groups, O and/or S and which can contain 1,4-phenylene groups, an aromatic C$_6$-C$_{30}$-hydrocarbon radical, which can be substituted by 1 to 4, substituents, which are selected from CH$_3$, —C$_2$H$_5$, —OH, —OCH$_3$ and/or —O—COCH$_3$, or a combination thereof;

X —COO—, —CON(R$^1$)— or is absent, wherein the bond to A takes place via O or N and wherein X is absent, if A is an aromatic hydrocarbon radical or CN;

B an aliphatic, linear or branched C$_1$-C$_{20}$-hydrocarbon radical, which can be substituted by 1 to 3 substituents, which are C$_1$- to C$_5$-alkyl and/or C$_1$- to C$_5$-alkoxy, which can be interrupted by 1 to 4 urethane groups, ester groups, O or S and which can contain 1 or 2 1,4-phenylene groups, an aromatic C$_6$-C$_{18}$-hydrocarbon radical, which can be substituted by 1 to 3 substituents comprising C$_1$- to C$_5$-alkyl and/or C$_1$- to C$_5$-alkoxy, tosyl or a combination thereof;

R$^1$ hydrogen or a linear or branched aliphatic C$_1$-C$_{10}$-hydrocarbon radical, which can be interrupted by 1 to 4 oxygen atoms and which can be substituted by 1 to 4 OH groups;

n an integer from 1 to 6.

12. Dental material according to claim 2, in which the variables of Formula 2 have the following meanings:

A an aliphatic linear or branched C$_1$-C$_{20}$-hydrocarbon radical, which can be interrupted by 1 to 4 1,4-phenylene groups, urethane groups, ester groups, O and/or S and which can be substituted by 1 to 4 OH groups, or a phenyl radical, which can be substituted by 1 to 3 substituents comprising —CH$_3$, and/or —OCH$_3$;

X —O—CO— or is absent, wherein the bond to A takes place via O and wherein X is absent, if A is an aromatic hydrocarbon radical or CN;

B an aliphatic linear or branched C$_1$-C$_{20}$-hydrocarbon radical, which can be interrupted by 1 to 4 oxygen atoms and which can contain 1 or 2 1,4-phenylene groups, or a phenyl radical, which can be substituted by 1 or 2, —OCH$_3$ or —CH$_3$ group(s);

n 1 or 2.

13. Dental material according to claim 1 in which the sulphonic acid ester is a compound of Formula 3,

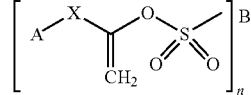

Formula 3 in which the variables have the following meanings:

A hydrogen, —CN, a phenyl radical, which can be substituted by 1 to 3 substituents comprising —CH$_3$, —C$_2$H$_5$, —OH, —OCH$_3$ and/or —O—COCH$_3$, or an aliphatic linear or branched C$_1$-C$_{20}$-hydrocarbon radical, which can be interrupted by 1 to 4 urethane groups, ester groups, O and/or S, which can contain 1 or 2 1,4-phenylene groups and which can be substituted by 1 to 4 OH groups;

B a cycloaliphatic, linear or branched aliphatic C$_1$-C$_{20}$-hydrocarbon radical, which can be substituted by 1 to 4 OH groups, which can be interrupted by 1 to 4 urethane groups, ester groups, O and/or S and which can contain 1 or 2 benzene groups, an aromatic C$_6$-C$_{18}$-hydrocarbon radical, which can be substituted by 1 to 4 OH groups, or a combination thereof;

X —COO— or —CON(R$^1$)— or is absent, wherein the bond to A takes place via O or N and wherein X is absent, if A is an aromatic hydrocarbon radical or CN;

R$^1$ hydrogen or a linear or branched aliphatic C$_1$-C$_{10}$-hydrocarbon radical, which can be interrupted by 1 to 4 oxygen atoms and which can be substituted by 1 to 4 OH groups;

n an integer from 2 to 4.

14. Dental material according to claim 4, in which the variables of Formula 3 have the following meanings:

A H, a phenyl radical, which can be substituted by one or more substituents comprising —$CH_3$, —OH, —$OCH_3$, or an aliphatic, linear or branched $C_1$-$C_8$-hydrocarbon radical, which can be interrupted by 1 to 4 urethane groups, ester groups and/or O;

B an aliphatic, linear or branched $C_1$-$C_{10}$-hydrocarbon radical, which can be interrupted by 1 to 4 O atoms and which can contain 1 to 4 1,4-phenylene groups, an aromatic $C_6$-$C_{10}$-hydrocarbon radical, or a combination thereof;

X —COO— or is absent, wherein the bond to A takes place via O and wherein X is absent, if A is an aromatic hydrocarbon radical or CN; and n 2.

15. Dental material according to claim 1, which comprises
    (a) 1.0 to 30 wt.-% of at least one compound of general formula 1,
    (b) 0.1 to 5.0 wt.-% initiator(s) for the radical polymerization, and optionally
    (c) 10 to 70 wt.-% multifunctional (meth)acrylate(s),
    in each case relative to the total mass of the dental material.

16. Dental material according to claim 1, which comprises
    (a) 2.0 to 30 wt.-% of at least one compound of general formula 1,
    (b) 0.1 to 3.0 wt.-% initiator(s) for the radical polymerization, and optionally
    (c) 10 to 60 wt.-% multifunctional (meth)acrylate(s),
    in each case relative to the total mass of the dental material.

17. Dental material according to claim 7 for use as prosthesis material, adhesive or coating material which comprises
    (a) 1.0 to 30 wt.-% of at least one compound of general formula 1,
    (b) 0.1 to 5.0 wt.-% initiator(s),
    (c) 10 to 80 wt.-% multifunctional (meth)acrylate(s),
    (d) 0 to 30 wt.-% monofunctional (meth)acrylate(s),
    (e) 0 to 3 wt.-% additive(s),
    (f) 0 to 50 wt.-% solvent comprising water, ethanol and/or polyethylene glycol,
    in each case relative to the total mass of the dental material.

18. Dental material according to claim 7 for use as prosthesis material, adhesive or coating material which comprises
    (a) 2.0 to 30 wt.-% of at least one compound of general formula 1,
    (b) 0.1 to 3.0 wt.-% initiator(s),
    (c) 15 to 80 wt.-% multifunctional (meth)acrylate(s),
    (d) 0 to 20 wt.-% monofunctional (meth)acrylate(s),
    (e) 0.2 to 3 wt.-% additive(s),
    (f) 0 to 40 wt.-% solvent comprising water, ethanol and/or polyethylene glycol,
    in each case relative to the total mass of the dental material.

19. Dental material according to claim 7 for use as composite, filling composite or cement, which comprises
    (a) 1.0 to 30 wt.-% of at least one compound of general formula 1,
    (b) 0.1 to 5.0 wt.-% initiator(s),
    (c) 10 to 40 wt.-% multifunctional (meth)acrylate(s),
    (d) 0 to 20 wt.-% monofunctional (meth)acrylate(s),
    (e) 20 to 85 wt.-% filler(s), and
    (f) 0 to 3 wt.-% additive(s),
    in each case relative to the total mass of the dental material.

20. Dental material according to claim 7 for use as composite, filling composite or cement, which comprises
    (a) 2.0 to 20 wt.-% of at least one compound of general formula 1,
    (b) 0.1 to 3.0 wt.-% initiator(s),
    (c) 10 to 30 wt.-% multifunctional (meth)acrylate(s),
    (d) 0 to 10 wt.-% monofunctional (meth)acrylate(s),
    (e) 30 to 80 wt.-% filler(s), and
    (f) 0.2 to 3 wt.-% additive(s),
    in each case relative to the total mass of the dental material.

* * * * *